(12) United States Patent
Cosgrove, III et al.

(10) Patent No.: US 10,285,712 B2
(45) Date of Patent: *May 14, 2019

(54) APPARATUS AND METHODS FOR OCCLUDING A HOLLOW ANATOMICAL STRUCTURE

(71) Applicants: IDX Medical, Ltd., Loveland, OH (US); The Cleveland Clinic Foundation, Cleveland, OH (US)

(72) Inventors: Delos M. Cosgrove, III, Hunting Valley, OH (US); Warren P. Williamson, IV, Loveland, OH (US); Craig B. Berky, Milford, OH (US)

(73) Assignees: Idx Medical, Ltd., Loveland, OH (US); The Cleveland Clinic Foundation, Cleveland, OH (US)

( * ) Notice: Subject to any disclaimer, the term of this patent is extended or adjusted under 35 U.S.C. 154(b) by 586 days.

This patent is subject to a terminal disclaimer.

(21) Appl. No.: 14/804,689

(22) Filed: Jul. 21, 2015

(65) Prior Publication Data

US 2015/0320426 A1   Nov. 12, 2015

Related U.S. Application Data

(60) Continuation of application No. 13/897,694, filed on May 20, 2013, now Pat. No. 9,119,627, which is a
(Continued)

(51) Int. Cl.
*A61B 17/04* (2006.01)
*A61B 17/122* (2006.01)
(Continued)

(52) U.S. Cl.
CPC ............ *A61B 17/122* (2013.01); *A61B 17/12* (2013.01); *A61B 17/1227* (2013.01);
(Continued)

(58) Field of Classification Search
CPC ....... A61B 17/12; A61B 17/29; A61B 17/122; A61B 17/128; A61B 17/1227; A61B 17/1285
See application file for complete search history.

(56) References Cited

U.S. PATENT DOCUMENTS 4,552,128 A * 11/1985 Haber ..................... A61F 2/004
128/DIG. 25
6,096,052 A * 8/2000 Callister .................. A61F 6/22
606/108

(Continued)

FOREIGN PATENT DOCUMENTS

WO   2005060838   7/2005

*Primary Examiner* — Tuan V Nguyen
(74) *Attorney, Agent, or Firm* — Wood Herron & Evans LLP

(57) ABSTRACT

A method of occluding an appendage of the heart with a clamp including at least first and second elongate clamping portions, the first and second elongate clamping portions including tissue engaging surfaces that promote tissue ingrowth. The method includes implanting the clamp by positioning the first and second elongate clamping portions on opposite sides of the appendage. At least one of the first or second elongate clamping portions is biased toward the other of the first and second elongate clamping portions to place the clamp into a clamping position on the appendage. Tissue ingrowth into the tissue engaging surfaces retains the clamp in place on the appendage.

7 Claims, 18 Drawing Sheets

Related U.S. Application Data division of application No. 12/632,293, filed on Dec. 7, 2009, now Pat. No. 8,465,507, which is a division of application No. 10/853,928, filed on May 26, 2004, now Pat. No. 7,645,285.

(51) Int. Cl.
*A61B 17/12* (2006.01)
*A61B 17/128* (2006.01)
*A61B 17/29* (2006.01)
*A61B 17/28* (2006.01)

(52) U.S. Cl.
CPC .......... *A61B 17/1285* (2013.01); *A61B 17/29* (2013.01); *A61B 2017/2825* (2013.01)

(56) References Cited

U.S. PATENT DOCUMENTS

| | | | | |
|---|---|---|---|---|
| 9,119,627 B2* | 9/2015 | Cosgrove | ................ | A61B 17/12 |
| 2002/0049457 A1* | 4/2002 | Kaplan | .................. | A61B 17/12 |
| | | | | 606/139 |
| 2004/0030335 A1* | 2/2004 | Zenati | ............... | A61B 17/12013 |
| | | | | 606/51 |
| 2004/0087987 A1* | 5/2004 | Rosenberg | ............. | A61B 17/12 |
| | | | | 606/157 |
| 2005/0149068 A1* | 7/2005 | Williams | ............. | A61B 17/122 |
| | | | | 606/151 |

* cited by examiner

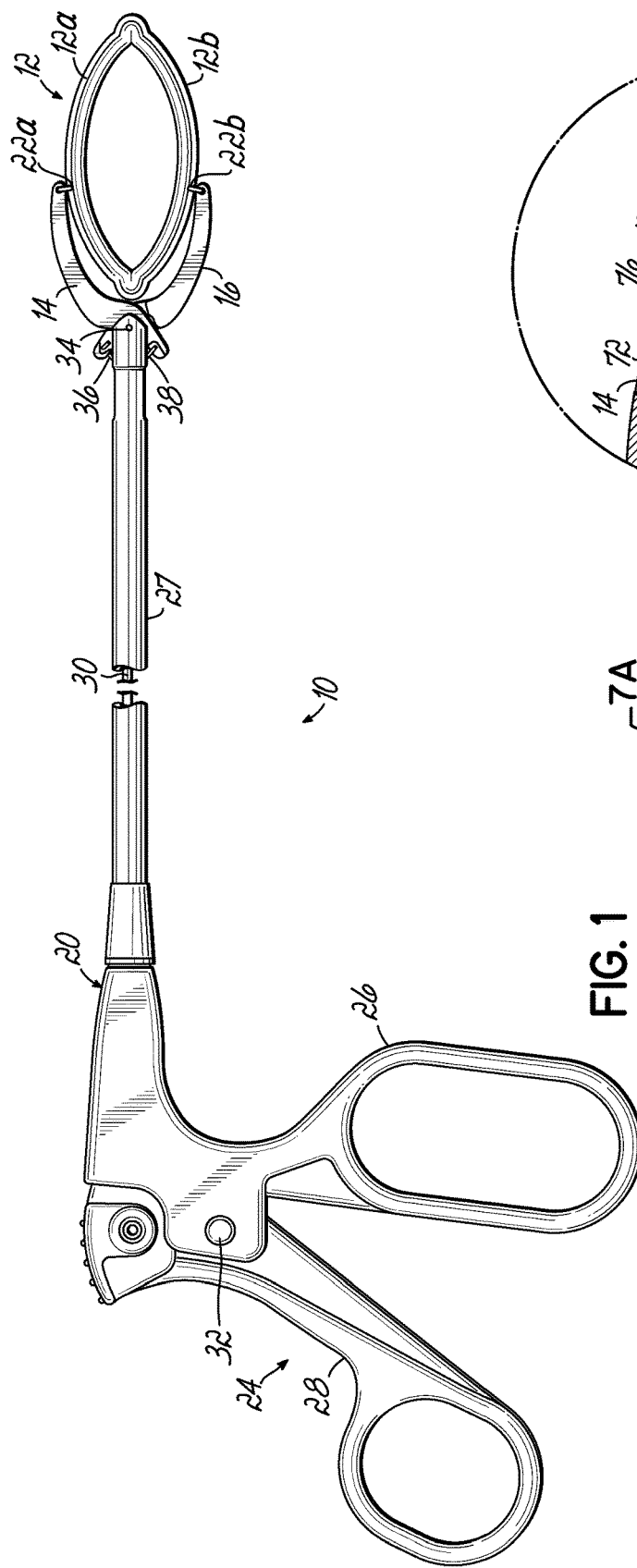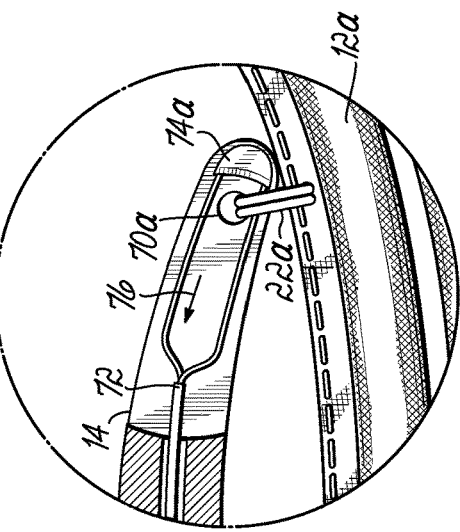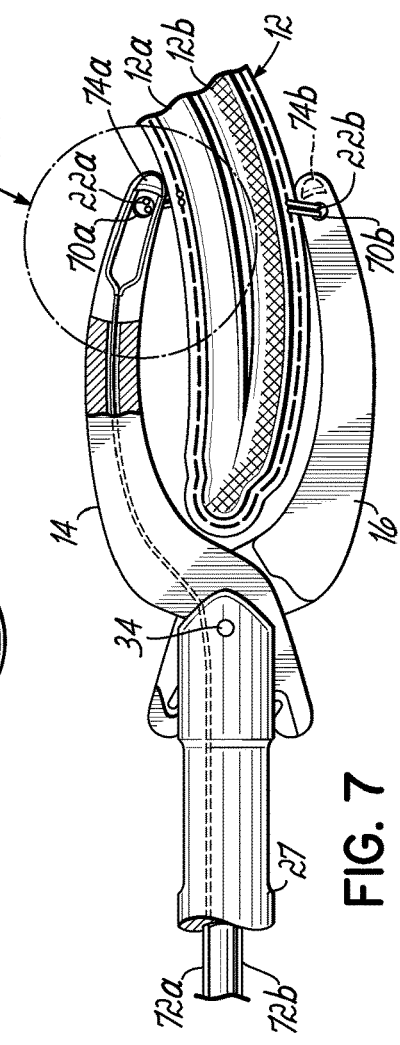
FIG. 1
FIG. 7A
FIG. 7

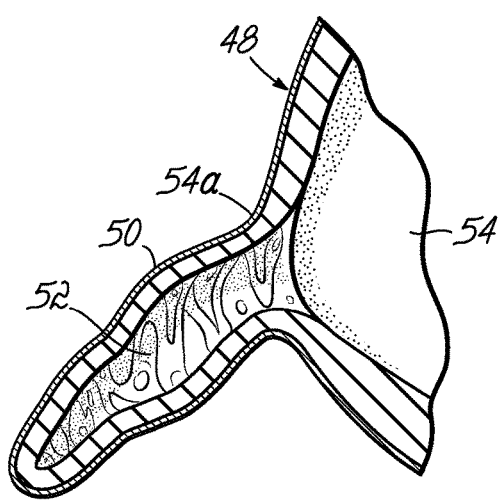
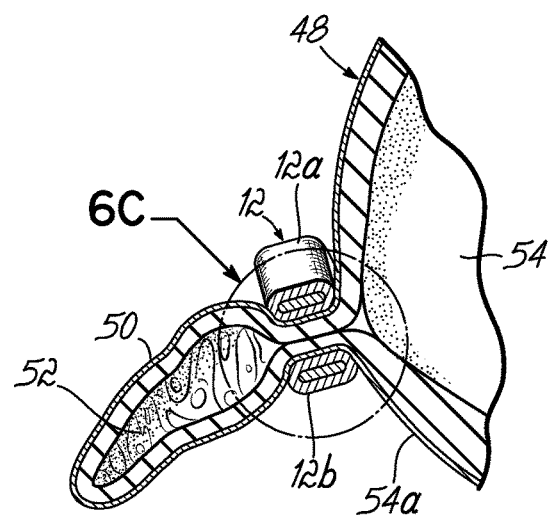
FIG. 6A    FIG. 6B
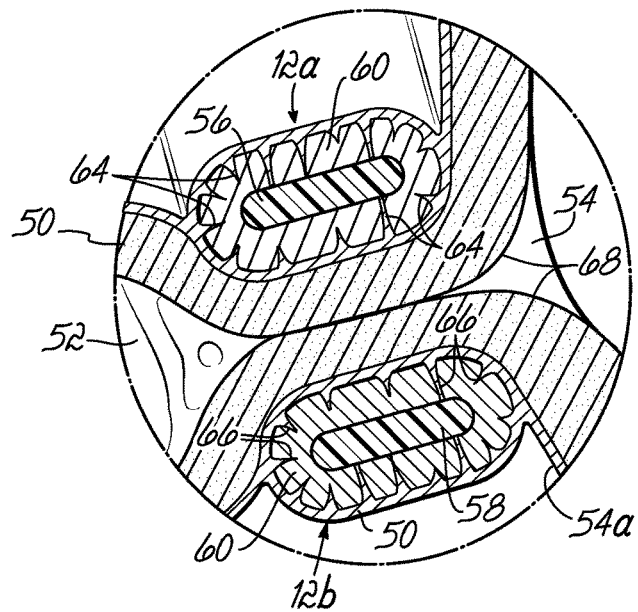
FIG. 6C

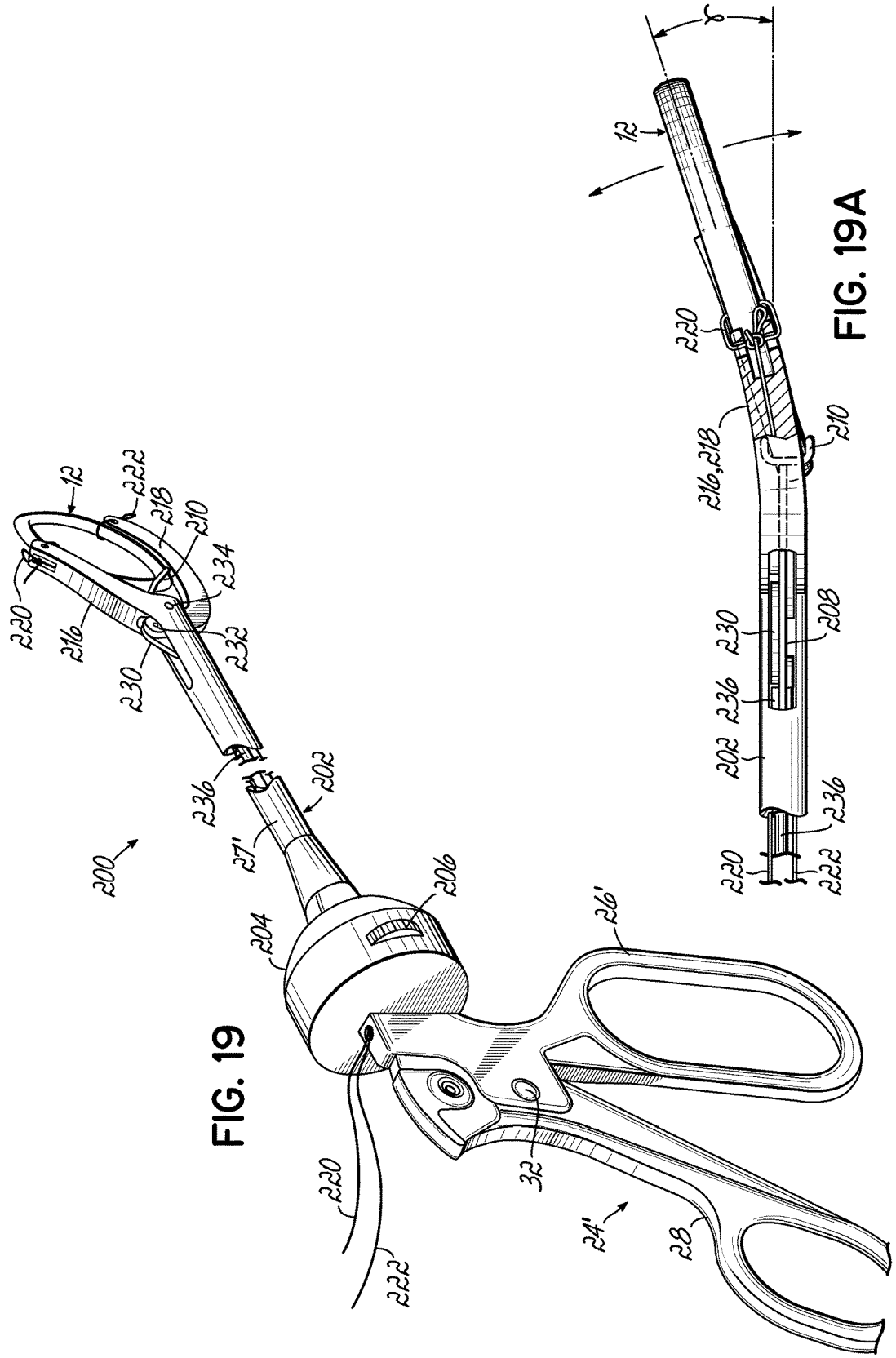

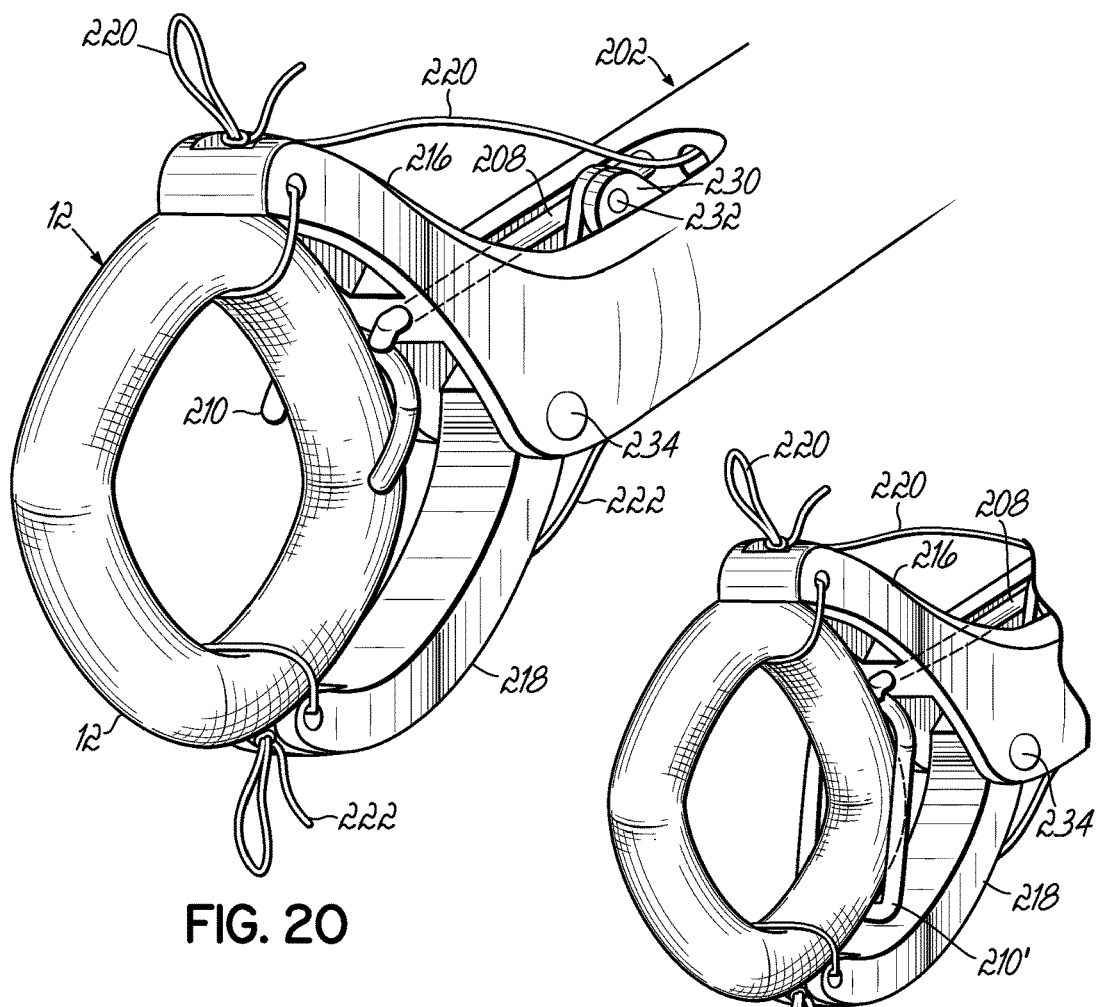
FIG. 20
FIG. 20A
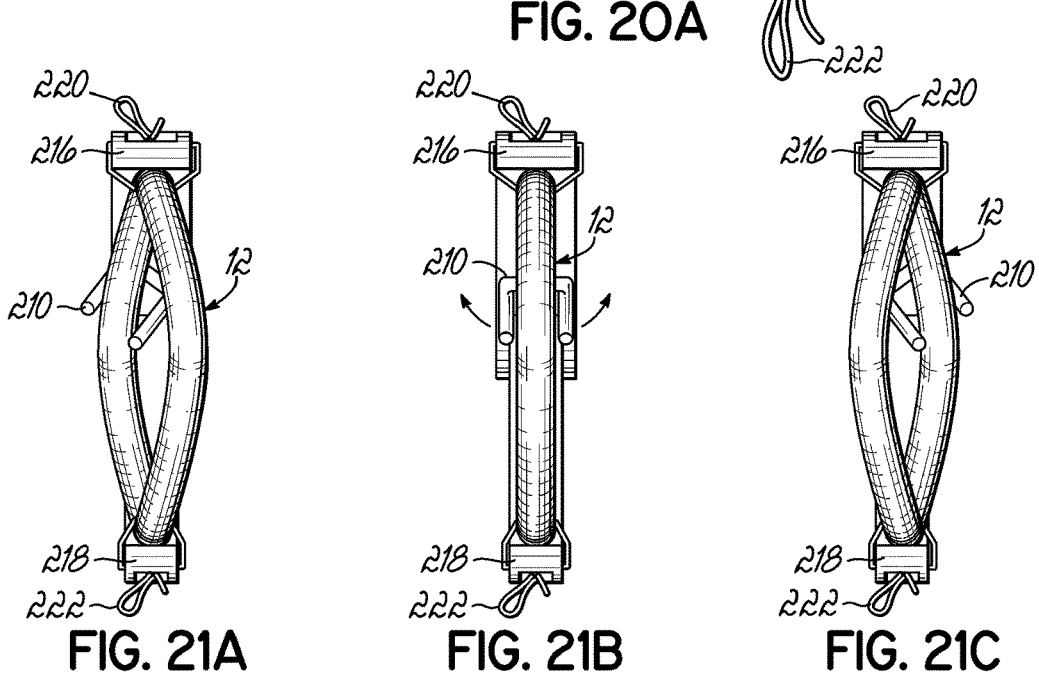
FIG. 21A FIG. 21B FIG. 21C

APPARATUS AND METHODS FOR OCCLUDING A HOLLOW ANATOMICAL STRUCTURE

CROSS REFERENCE TO RELATED APPLICATIONS

This application is a continuation of Ser. No. 13/897,694, filed May 20, 2013 (now U.S. Pat. No. 9,119,627) which is a divisional of Ser. No. 12/632,293, filed Dec. 7, 2009 (now U.S. Pat. No. 8,465,507), which is a divisional of Ser. No. 10/853,928, filed May 26, 2004 (now U.S. Pat. No. 7,645,285), the disclosures of which are hereby fully incorporated herein by reference.

FIELD OF THE INVENTION

The present invention relates generally to surgical methods and apparatus for occluding a hollow tissue structure, such as when occluding vessels, or pedunculated structures such as an appendix, gall bladder or appendages on the heart. More specifically, the present invention relates to a method and device for occluding the left atrial appendage of the heart in either an open surgical procedure or minimally invasive procedure.

BACKGROUND OF THE INVENTION

Atrial fibrillation is a common cardiac rhythm disorder that affects more than two million people each year. Until relatively recently, atrial fibrillation was thought to be a nuisance arrhythmia with few consequences. However, recent medical research has uncovered some devastating complications including cardiomyopathy, congestive heart failure and stroke.

During atrial fibrillation the upper part of the heart beats (quivers) faster than the rest of the heart. This phenomenon is due to the generation of erratic or extra electrical signals which cause the top part of the heart to quiver rapidly and irregularly (fibrillate) as many as 300-600 times a minute. However, the entire heart does not beat that fast. The heart is a muscular pump divided into four chambers, two atria on the top of the heart and two ventricles on the bottom portion of the heart. Normally, the heartbeat starts in the right atrium when a special group of cells sends an electrical signal. These cells are called the sinoatrial or SA node, sinus node or the heart's "pacemaker". The signal spreads throughout the atria and to the atrioventricular or AV node. The AV node connects to a group of fibers in the ventricles that conduct the electrical signal. The electrical impulse travels via these specialized fibers to all parts of the ventricles. The specialized fibers are also known as the His-Purkinje system. The electrical signal must follow this exact route for the heart to pump properly. Normally, the heart beats at 60-80 times per minute at rest. This number represents the contractions of the lower heart or ventricles. During atrial fibrillation, electrical signals from other parts of the heart disrupt the heart's normal rhythm and cause the atria to quiver or beat too fast. However, only a small number of these atrial beats make it through the AV node, which acts like a gate to the ventricles. This is fortunate, because a rapid ventricular heartbeat would be much more dangerous and potentially fatal. However, some atrial fibrillation does make it through the AV node making the heart beat faster than normal. An atrial fibrillation attack is usually not life threatening. The most significant danger is stroke.

Blood usually moves completely through the chambers of the heart. During atrial fibrillation, the heart is not pumping normally or efficiently. The blood begins to pool in the atria and this stagnation of blood can cause the blood to thicken and form clots. These clots are then ejected out of the heart and into the bloodstream where they can lodge in the brain causing a stroke. Atrial fibrillation can make stroke five times more likely than in the general population. When the heart experiences atrial fibrillation there may not be enough blood pumping to the brain or other organs. This can cause dizziness, shortness of breath or organ failure. Untreated atrial fibrillation will also weaken the heart due to phenomenon known as remodeling. The heart, like the rest of the body, adapts to changes. The fast abnormal rhythm in the atria causes electrical changes, and this can enlarge the heart.

There are three major objectives in the treatment of atrial fibrillation: the restoration of normal sinuous rhythm, control of ventricular rate during atrial fibrillation, and the prevention of blood clot formation. Some methods of treatment for atrial fibrillation include pharmacological therapy, pacemakers, and surgery.

For the prevention of blood clots, research has demonstrated that the anticoagulation warfarin (e.g., Coumadin) is effective in reducing the risk of blood clot formation and stroke but it does not totally eliminate the risk. An anticoagulant such as warfarin interferes with the body's natural clotting mechanism. The dosage of warfarin is highly individualized and must be carefully monitored with blood tests to ensure safety. While this pharmacological treatment may significantly reduce the risk of stroke, it also increases the risk of bleeding and may be inappropriate for many atrial fibrillation patients.

As an alternative to pharmacological therapy, there are a few surgical procedures that isolate the left atrial appendage from the blood's circulatory system. The most common approach is to occlude the left atrial appendage during open-heart surgery. In open heart surgery the patient is placed on a heart-lung bypass machine and the heart is temporarily isolated from the circulatory system while the surgeon operates on the heart. The left atrial appendage is a small hollow extension (i.e., a pedunculated structure) formed off the lateral wall of the left atrium. It has been referred to as a small windsock or a small, flat hollow finger-like protrusion. The left atrial appendage usually contracts with the rest of the left atrium during normal heart function thereby continually moving blood throughout the hollow extension. During atrial fibrillation, the left atrial appendage often fails to contract thereby allowing the blood to pool inside the appendage, becoming stagnated. As a result, the blood becomes thicker and thrombus or clot formation begins. These clots can be slowly ejected from the left atrial appendage into the left atrium and left ventricle, and then released into the bloodstream thereby becoming an obstruction in the brain or other vascular structures. For this reason, it is advantageous to prevent these clots from forming and being dislodged into the bloodstream. One method of preventing the occurrence of clots is to occlude the appendage thus preventing blood from entering and forming clots. This also prevents clots already formed in the appendage from escaping into the bloodstream. Normally, the occlusion of the left atrial appendage is performed in conjunction with other procedures such as a mitral valve replacement or coronary artery bypass procedure and not as the sole reason for the procedure.

There are several different methods being used today to occlude the left atrial appendage. One method is percutaneous left atrial appendage transcathether occlusion. A small occlusion device is deployed from a venous access catheter into the left atrium and blocks the opening into the atrial appendage. In order to access the left atrium from the vena cava's right atrium, the surgeon must go through the atrial wall. Many surgeons are uncomfortable with making an opening in this wall without being able to repair it at the end of the procedure. There are also issues of placing an occlusion device inside the heart. If the occlusion device becomes detached within the heart, the result may be fatal.

Another method of occlusion is placing a loop around the left atrial appendage and cinching it down in a manner similar to a garrote. When trying to place a flaccid loop around an irregular pedunculated structure, it can be difficult to make certain the loop is positioned at the base of the appendage. When cinching the loop, it is very easy to over tighten the loop, and this can result in severing the delicate atrial appendage. Even a partial tear can create problems in getting access to repair the tear. This method of occlusion may not always seal the opening between the appendage interior and the atrium. That is, there may still be a partial opening due to the way the appendage wall collapses during cinching of the loop. Such a partial opening could still allow some flow into and out of the atrial appendage, leading to the problems mentioned above. In addition, transforming the relatively flat structure of the appendage onto a round hard mass, as does a cinching method, could lead to other problems.

Another method of occlusion is to place a linear surgical stapler at the base of the appendage and a left atrial wall and stapling the appendage closed. Due to the limited access, the ability to visualize the entire atrial appendage while placing the stapler in the correct location can be a problem. It is very difficult to make certain the staple line makes a complete occlusion of the appendage. Again, a partial occlusion of the appendage can still result in the formation and dislodgement of clots.

For the aforementioned reasons, it would be desirable to provide improved methods and devices to reliably occlude hollow anatomical structures, and especially the left atrial appendage of the heart completely and safely. Such methods may be performed during an open-heart surgical procedure such as a valve replacement or coronary artery bypass. It would also be desirable to provide methods and devices that may be used in a minimally invasive procedure while the heart is beating without placing the patient on a heart-lung bypass machine. A minimally invasive device would allow access through either an intercostal space between the ribs or a supra and/or sub-xiphoid approach to gain access to the left atrial appendage. Such devices will allow complete visualization of the left atrial appendage for the surgeon and permit minor placement adjustments to be made before permanent installation is made. The devices would also allow complete occlusion of the left atrial appendage, eliminating the risk of clots forming in the appendage, traveling throughout the bloodstream, and possibly lodging in the brain causing a stroke.

SUMMARY OF THE INVENTION

The present invention provides devices and methods for occluding a hollow anatomical structure, such as the left atrial appendage of the heart. Generally, the device comprises a clamp having at least first and second clamping portions adapted to be placed on opposite sides of the hollow anatomical structure. At least one of the first and second clamping portions is movable toward the other of the first and second clamping portions from an open position into a clamping position to occlude the hollow anatomical structure. The clamp comprises a closed, annular shape configured to surround the hollow anatomical structure in the open position and then assumes a flattened shape in the clamping position to occlude the hollow interior of the hollow anatomical structure. The first and second clamping portions can further comprise concave portions curved in opposite directions to form the clamp into a generally oval shape.

In various embodiments, at least one of the first and second clamping portions is spring biased toward the other of the first and second clamping portions in the clamping position. In this regard, one clamping portion may be normally spring biased toward the other of the first and second clamping portions when the first and second clamping portions are in the open position. Upon release, the spring biased clamping portion moves toward the other clamping portion into a clamping or occluding position. In another embodiment, one of the first and second clamping portions is movable toward the other of the first and second clamping portions to an over-center position at which a spring bias takes effect and moves the one clamping portion toward the other clamping portion to the clamping position.

In another aspect of the invention, the first and second clamping portions have tissue engaging surfaces for engaging the hollow anatomical structure in the clamping position. The tissue engaging surfaces are roughened and preferably adapted to promote tissue ingrowth. The tissue engaging surfaces may be comprised of a fabric covering on at least one of the first and second clamping portions. Other manners of promoting tissue ingrowth may be used on one or both clamping portions such as etching and other pore-creating methods such as metal deposition. Pore size should preferably range from 200-400 microns. A protective overmold may be provided of, for example, silicone to assist with traction if tissue ingrowth feature is not utilized on one or both clamping portions. Alternatively, and if necessary, silicone overmolding or other protective guards may be used to prevent irritation of surrounding tissue, while clamping areas of the device may be designed to promote traction and/or tissue ingrowth such as described above.

In another aspect, the first and second clamping portions have complementary shapes in cross section such that the complementary shapes fit together in the clamping position. At least one of the first and second clamping portions may be convexly curved toward the other of the first and second clamping portions in cross section. This feature may assist with providing more uniform force distribution and/or more sealing force along the length of the clamp.

In another aspect, projections may be provided on at least one of the first and second clamping portions. The projections are configured to engage and, optionally, pass through the hollow anatomical structure when the clamp is in the clamping position. The projections thereby assist with retention of the clamp on the tissue. To further assist with clamp retention, receiving elements may be provided on the opposing clamping portion to engage and lock with the projections when the clamp is in the clamping position. Other types of locking elements may be provided, such as ratchet elements, undulations on tissue engaging areas, bands on the outside of the clamp or other suitable structure.

The clamp may also have an actuating element configured to move one of the first and second clamping portions toward the other of the first and second clamping portions. This may, for example, be one or more magnetic elements on one or both clamping portions, or a mechanical actuation element such as a rotating or sliding cam element, or any other suitable actuation mechanism.

The invention also provides apparatus for occluding a hollow anatomical structure which includes a clamp delivery and actuation device. In the preferred embodiment, the delivery and actuation device includes first and second jaws, and an actuator configured to move at least one of the first and second jaws toward the other of the first and second jaws. The clamp delivery and actuation device preferably includes a pistol grip with an actuating member configured to be manually depressed to move one of the first and second jaws toward the other of the first and second jaws. The first and second clamping portions are secured between the first and second jaws and may be moved from the open position to the clamping position by moving at least one of the first and second jaws. This allows the clamp to be repeatedly opened and closed, as necessary for repositioning purposes, during the surgical procedure. The clamp may be secured to the jaws in any suitable manner, such as by using suture or by using other types of gripping elements. The delivery and actuation device preferably carries a mechanism to release the clamp, such as a blade to cut the suture, or a tension member which may be pulled to release the gripping elements or suture. In the case of using the suture, the tension member may be used to untie the suture, and may be an end of the suture itself.

The clamp is preferably coupled to the first and second jaws so as to pivot about an axis generally transverse to its length. This pivoting action may take place passively or actively. To provide for active or selective pivoting of the clamp, as may be desired by a surgeon to more accurately position the clamp, the delivery and actuation device includes a pivoting mechanism coupled to the clamp and configured to pivot the clamp in opposite directions about the axis. The surgeon may operate the pivoting mechanism at the proximal or handle end of the device.

The invention further provides methods for occluding a hollow anatomical structure with an annular clamp having at least first and second clamping portions. Generally, the method comprises surrounding the hollow anatomical structure with the annular clamp, and then moving at least one of the first and second clamping portions toward the other of the first and second clamping portions to occlude the hollow anatomical structure. In the preferred embodiment, the hollow anatomical structure is a pedunculated organ or portion of an organ. Most specifically, it is the left atrial appendage of a heart. Preferably, the method involves accessing the left atrial appendage of the heart by a mini-thoracotomy or by another minimally invasive approach.

The method preferably further comprises engaging a structure configured to promote tissue ingrowth, such as a fabric covering, with the hollow anatomical structure, and optionally also engaging the anatomical tissue with projections to promote tissue ingrowth after clamping has taken place. The clamp may be passively or actively pivoted with respect to the delivery device prior to the step of moving at least one of the first and second clamping portions toward the other. In another aspect, a tissue gripper with flat, paddle-shaped gripper elements is provided and used to gently grasp and pull the tissue through the clamp when the clamp is in the open, annular configuration.

It will be appreciated that various additional aspects of the methods carried out by the various embodiments of this invention will be readily apparent based on the use of the devices and components of the clamp and the delivery and actuation device as described hereinabove and further below.

The present invention provides improved devices and methods for occlusion of hollow tissue such as the left atrial appendage. One advantage of various embodiments described herein is that the surgeon can open and close the clamp if needed to change the position of the clamp for a better result prior to release of the clamp onto the tissue. The configuration of the delivery and actuation device is such that the device can be used not only in an open surgical procedure, but in a minimally invasive surgical procedure during which, for example, the device is placed between or under the patient's ribs for access to the left atrial appendage. The implantable clamp has a geometry which traps appendage tissue within an annular opening thereby positively attaching the clamp to the tissue.

In another embodiment, the invention contemplates an apparatus for occluding a hollow anatomical structure comprising a clamp delivery and actuation device including a hollow structure containing a clamp deploying member. The apparatus further includes a clamp having at least first and second clamping portions adapted to be placed on opposite sides of the hollow anatomical structure. At least one of the first and second clamping portions is movable toward and away from the other of the first and second clamping portions between a closed position and an open position in which the clamp assumes an annular shape. The clamp is carried within the hollow structure in the closed position and is extendable out of the hollow structure by the deploying member whereupon the clamp may be actuated to the open position and clamped onto the hollow anatomical structure. This embodiment is especially useful for minimally invasive surgical procedures.

These and other features, objects and advantages of the invention will become more readily apparent to those of ordinary skill in the art upon review of the following detailed description, taken in conjunction with the accompanying drawings.

BRIEF DESCRIPTION OF THE DRAWINGS

FIG. 1 is a side elevational view of an apparatus constructed in accordance with the invention including a clamp and a delivery and actuation device.

FIG. 6A is a cross sectional view illustrating the left atrial appendage and a portion of the heart.

FIG. 6B is a cross sectional view similar to FIG. 6A, but illustrating the application of a clamp to the left atrial appendage according to the invention.

FIG. 6C is an enlarged view of the encircled portion 6C shown in FIG. 6B.

FIG. 7 is a partially cross sectioned side elevational view of the jaws and clamp shown in FIG. 1, partially sectioned to illustrate a clamp release feature.

FIG. 7A is an enlarged view of encircled portion 7A shown in FIG. 7.

FIG. 19 is a perspective view illustrating an alternative apparatus including a clamp and delivery and actuation device.

FIG. 19A is a top view of the distal end of the device shown in FIG. 19.

FIG. 20 is a perspective view of the distal end of the device shown in FIGS. 19 and 19A.

FIG. 20A is a perspective view similar to FIG. 20 but illustrating an alternative yoke design for the clamp pivoting mechanism.

FIGS. 21A-21C are respective front elevational views illustrating the operation of the clamp pivoting mechanism shown in FIG. 20.

DETAILED DESCRIPTION

Figure 2A:
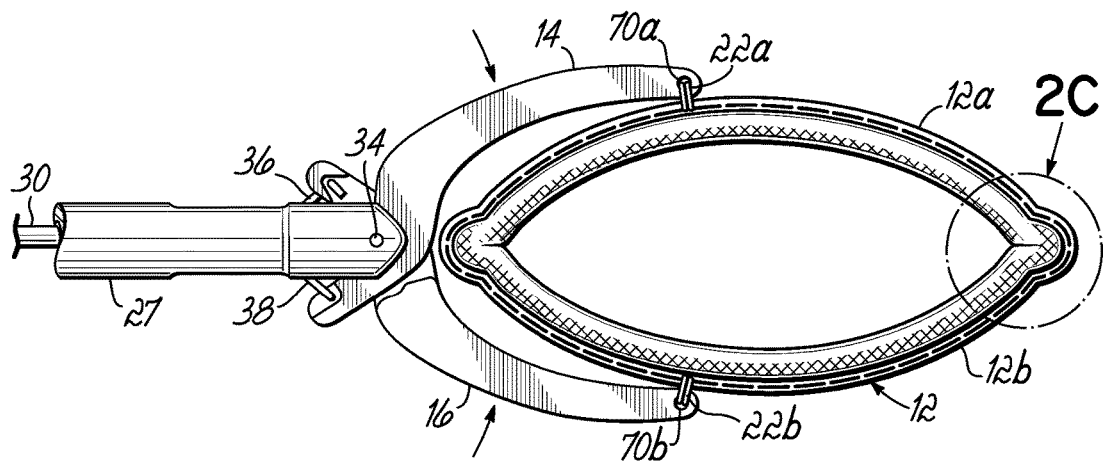
FIG. 2A is an enlarged side elevational view of the clamp and jaws shown in FIG. 1, with the clamp in an open position.

Referring initially to FIGS. 1, 2A, 2B and 3, a first embodiment of the invention includes an apparatus 10 comprising a clamp 12 having respective first and second clamping portions 12a, 12b secured between first and second jaws 14, 16. A delivery and actuation device 20 carries first and second jaws 14, 16 for actuating clamp 12 between open and closed or clamping positions as will be described further below. Clamp portions 12a, 12b are secured to jaws 14, 16 by respective sutures 22a, 22b. Delivery and actuation device 20 includes a pistol grip 24 having a stationary handle 26 coupled with an elongate jaw support member 27. A movable handle 28 is coupled with an actuating bar 30 and pivots with respect to stationary handle 26 at a pivot member 32. When movable handle 28 is depressed toward stationary handle 26, this action draws actuating bar 30 to the left as viewed in FIG. 1. Actuating bar 30 has a connecting portion 30a secured to respective rigid wire members 36, 38. Wire members 36, 38 are secured to jaws 14, 16 such that when wire members 36, 38 are pulled by actuating bar 30, jaws 14, 16 pivot toward each other about pivot member 34. This moves clamping portion 12a to an over-center position with respect to clamping portion 12b whereupon clamping portion 12a snaps into the clamping position shown in FIG. 2B.

Figure 2B:
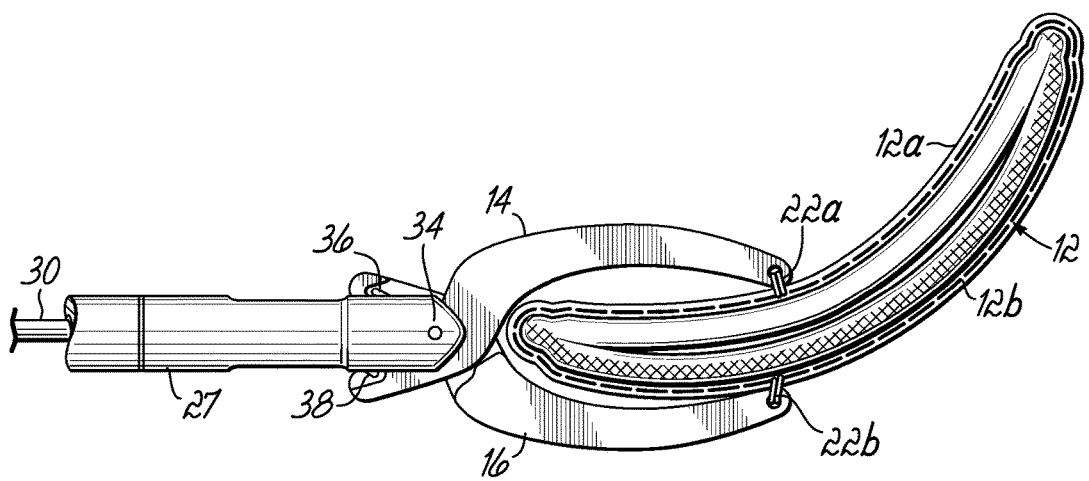
FIG. 2B is an enlarged side elevational view similar to FIG. 2A, but illustrating the clamp in a closed or clamping position.
Figure 3:
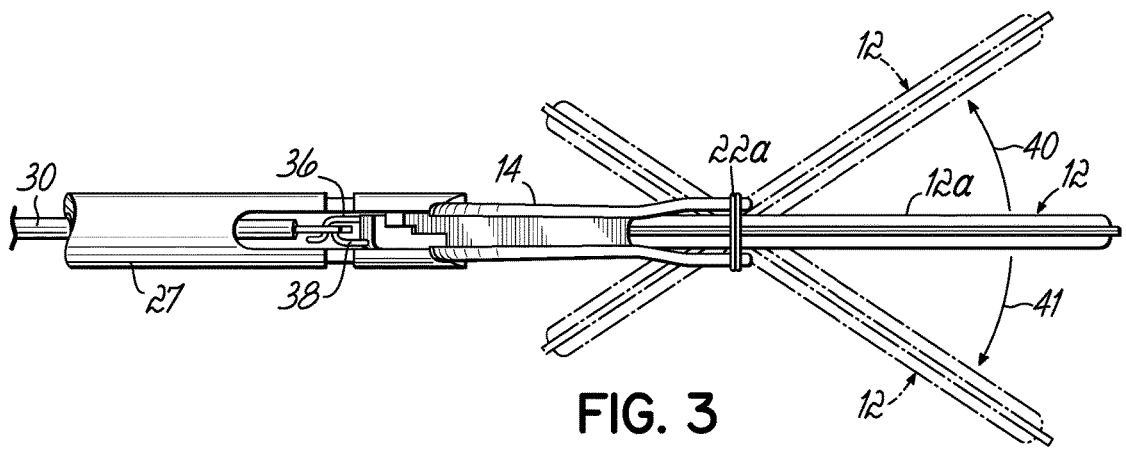
FIG. 3 is a top view of the clamp and jaws shown in FIGS. 2A and 2B, illustrating the pivotal action of the clamp.

Thus, it will be appreciated that the clamp 12 changes from the generally oval, annular (i.e., closed ring-shape) shape shown in FIG. 2A to the flattened, curved shape shown in FIG. 2B when moving from the open to the closed position. It will also be appreciated with respect to this embodiment and others disclosed herein that clamp 12 may be repeatedly opened and closed by device 20. This can allow repositioning of clamp 12, as necessary, during the surgical procedure prior to release of clamp 12 from device 20. FIG. 3 further illustrates that clamp 12 is pivotal about an axis extending transverse to the length of clamp 12 in opposite directions as shown by arrows 40, 41. This pivoting action is a passive pivoting action. That is, clamp 12 may freely pivot from the generally straight orientation shown in solid lines to the respective oppositely angled orientations shown in dash-dot lines.

Figure 2C:
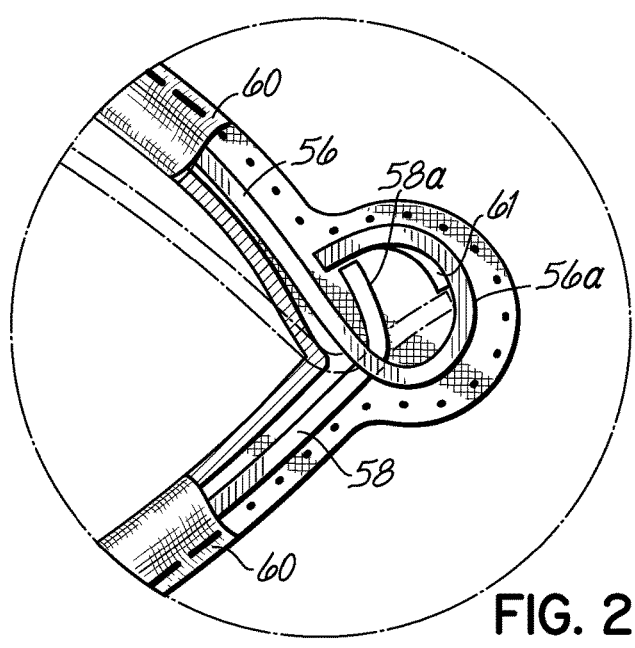
FIG. 2C is an enlarged view of encircled portion "2C" of FIG. 2A with the fabric covering broken away.

FIG. 2C illustrates, in enlarged detail, an end portion of clamp 12 with a fabric covering 60 partially removed to reveal leaf spring members 56, 58, which operate as will be discussed below. As shown in FIG. 2C, leaf spring member 56 includes a rounded end portion 56a which is designed to protect the patient from irritation which may have otherwise been caused by exposed sharp edges of leaf springs 56, 58. FIG. 2C also illustrates an end portion 58a of leaf spring member 58 which is angled relative to the remaining portion of leaf spring member 58 and is positioned inside of rounded end portion 56a. A stop tab 61 is also formed in rounded end portion 56a, such as through a stamping operation. As leaf spring member 58 moves from the open position (shown in solid lines) to the closed position (shown in dash-dot lines), angled end portion 58a will rotate against and finally stop behind tab 61 to lock leaf spring member 58a in the closed position.

Figure 4A:
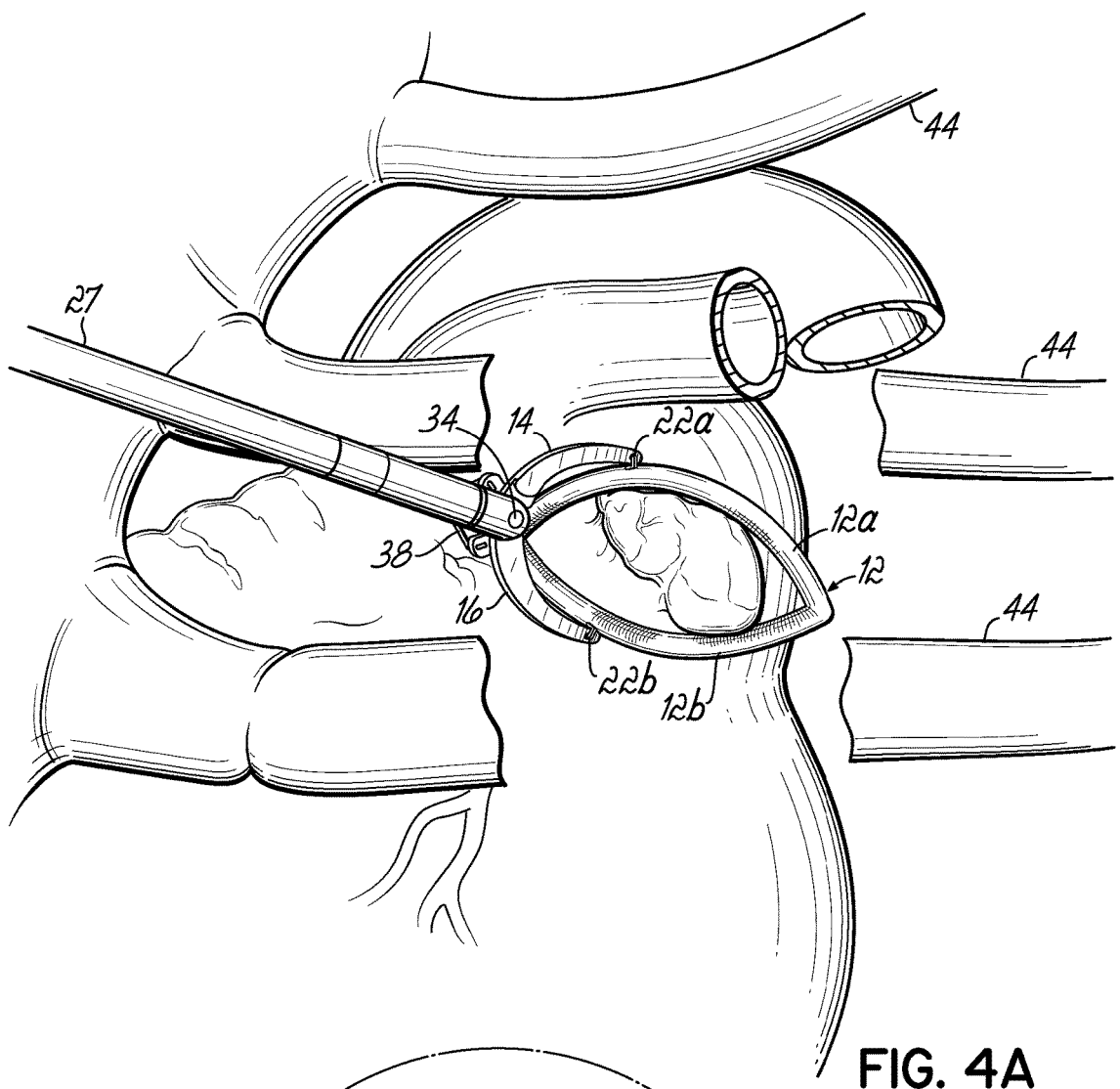
FIG. 4A is a partially fragmented perspective view illustrating the clamp being applied to the left atrial appendage of the heart.
Figure 4B:
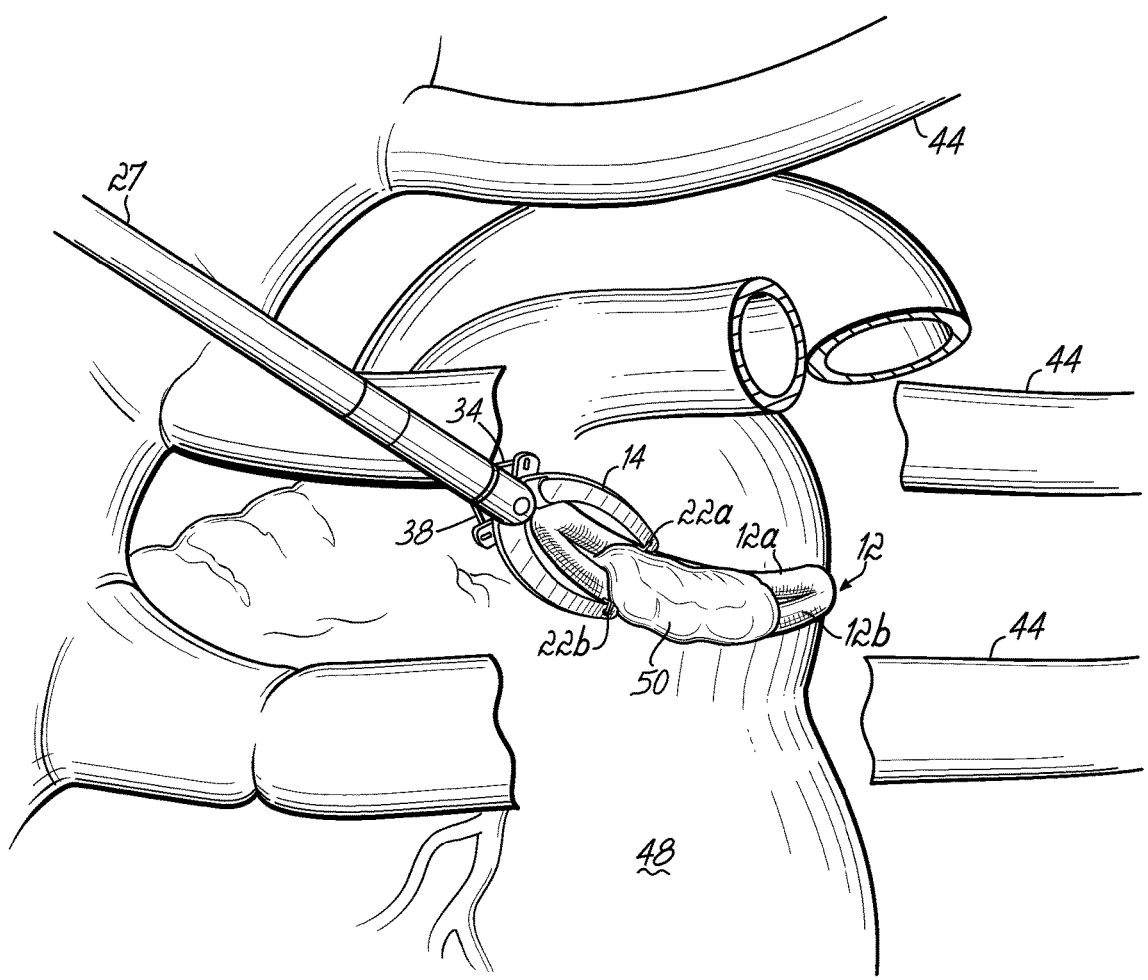
FIG. 4B is a perspective view similar to FIG. 4A, but illustrating the clamp in a closed position on the left atrial appendage.

FIGS. 4A and 4B partially illustrate the chest anatomy of a patient comprising ribs 44 and a heart 48 including a left atrial appendage 50. In one approach using the present invention, clamp 12 may be delivered medially between respective ribs 44 through, for example, a thoracotomy and intercostal space. In this regard, a relatively small incision (not shown) is made between ribs 44 and clamp 12, jaws 14, 16 and elongate jaw support member 27 are directed between ribs 44 through the incision. The opened clamp 12 may be placed around left atrial appendage 50 such that clamping portions 12a, 12b, which form an annular shape, surround left atrial appendage 50 as shown in FIG. 4A. As further shown in FIG. 4B, when jaws 14, 16 are actuated to a closed position as previously described, clamping portions 12a, 12b move together essentially as shown to clamp and close off or occlude left atrial appendage 50.

Figure 5:
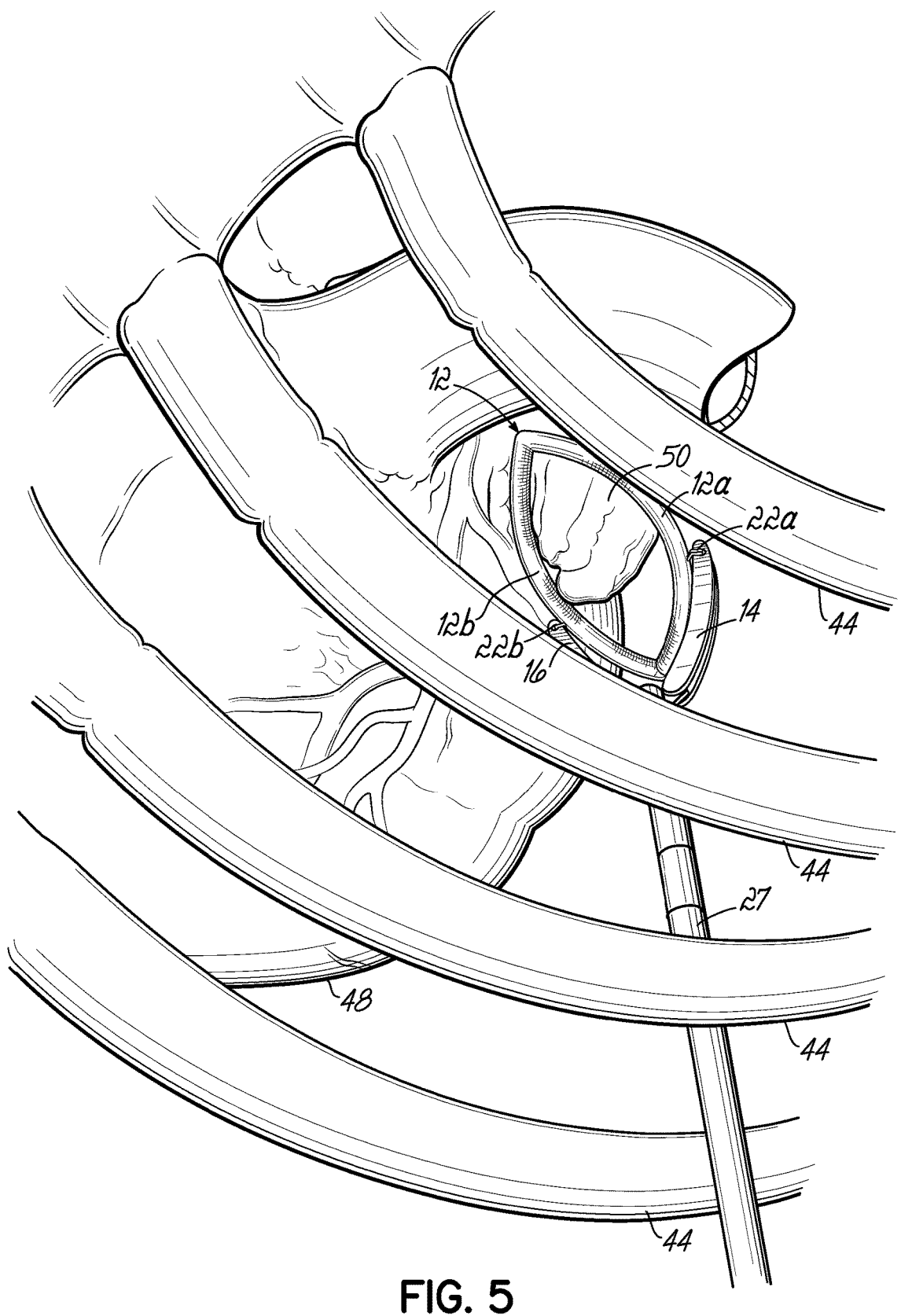
FIG. 5 is a perspective view similar to FIG. 4A, but illustrating a lateral approach of the clamp onto the left atrial appendage.

FIG. 5 illustrates one of several other approaches which may be used with the present invention. In this regard, clamp 12, jaws 14, 16, and elongate jaw support member 27 may be introduced in an intercostal space between a patient's ribs 44 using a lateral approach to thereby access the left atrial appendage 50. After suitably angling clamp 12 and surrounding left atrial appendage 50 with clamping portions 12a, 12b, jaws 14, 16 may be actuated as previously described to bring clamping portions 12a, 12b together and close off left atrial appendage 50. It will be appreciated that a sub-xiphoid approach may also be used, as well as several other approaches, such as open surgical approaches used during open heart surgery.

FIGS. 6A, 6B and 6C illustrate schematic cross sections of a portion of heart 48. In particular, left atrial appendage 50 is shown in cross section to illustrate its hollow interior 52 which communicates with the left atrium 54 of heart 48. FIG. 6A illustrates the normal configuration of left atrial appendage 52. FIG. 6B illustrates clamp 12 in place, with FIG. 6C illustrating the same in enlarged detail. As shown in FIGS. 6B and 6C, clamping portions 12a, 12b respectively comprise clamp members 56, 58, at least one of which acts as a leaf spring member, and having a fabric covering 60 thereon. Fabric coverings may be treated with collagen, albumin, etc., to promote tissue ingrowth 64, 66. Fabrics such as DACRON polyester or expanded polytetrafluoroethylene may be used in this regard to promote inflammatory response and tissue ingrowth. Such tissue ingrowth 64, 66 will then assist with retaining clamp 12 in place. Clamp 12 may be placed extremely close to the outer surface 54a of left atrium 54 to ensure that there is very little void space at junction 68 (FIG. 6C). Elimination of void space is important, for example, to ensure that blood clots do not form from stagnant blood.

FIGS. 7 and 7A illustrate one embodiment of a mechanism used for releasing clamp 12 from jaws 14, 16. Specifically, sutures 22a, 22b may be tied through apertures 70a, 70b. Respective tension members 72a, 72b are coupled to blades 74a, 74b. When tension members 72a, 72b are pulled proximally (see arrow 76 in FIG. 7A), blades 74a, 74b move past apertures 70a, 70b and cut sutures 22a, 22b. Optionally, sutures 22a, 22b may be formed as a single suture such that a single blade may be used to release the clamp 12 and the entire suture may be then carried out of the patient with one of the jaws 14, 16. In the embodiment shown, in which both sutures 22a, 22b are cut, the sutures 22a, 22b may, for example, remain tied to clamp portions 12a, 12b.

Figure 8A:
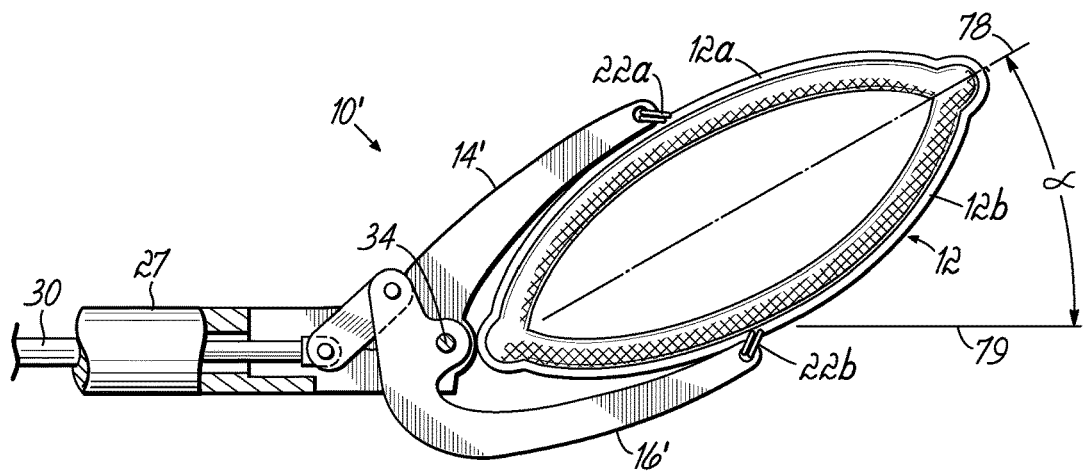
FIG. 8A is a side elevational view of a clamp and alternative jaw orientation for the clamp delivery and actuation device, with the clamp shown in an open position.
Figure 8B:
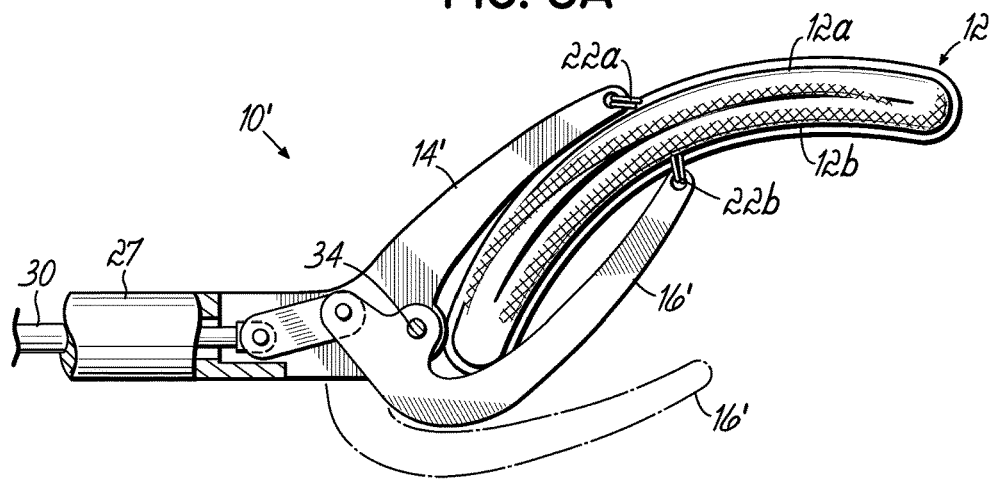
FIG. 8B is a side elevational view similar to FIG. 8A, but illustrating the clamp in a closed or clamping position.

FIGS. 8A and 8B respectively illustrate the open and closed positions of an alternative apparatus 10' constructed in accordance with the invention. In this embodiment, like reference numerals are used to indicate like components of the first embodiment described above. Therefore, these like components need no additional explanation. Components having reference numerals with prime marks (') indicate components which have been slightly modified in this embodiment as will be apparent. In this regard, all components of apparatus 10' may be as described previously, except that jaws 14', 16' are angled such that they hold clamp 12 at an acute angle α relative to the axis of elongate jaw support member 27. That is, the length of clamp 12 extends along an axis 78 which forms an angle of in the range of approximately 20°-30° with respect to axis 79 of elongate jaw support member 27. This angled delivery orientation of clamp 12 has been found to enable easier application of clamp 12 to the left atrial appendage 50 (FIG. 4A). An additional angle γ may also be utilized as viewed from the top and discussed relative to FIG. 19A below. In all other respects, the operation of apparatus 10' may be the same as described above.

Figure 9:
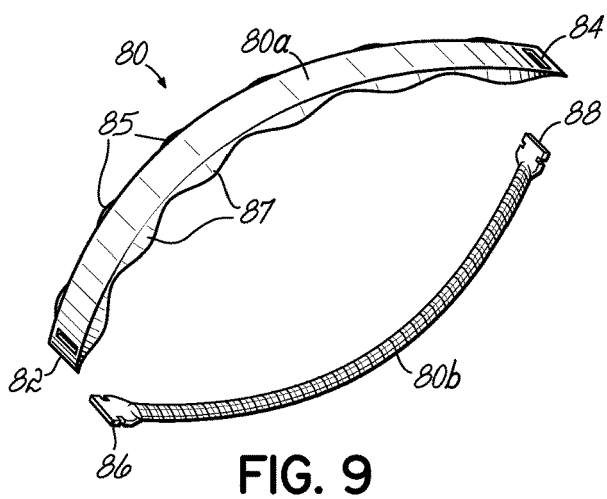
FIG. 9 is a disassembled perspective view of an alternative clamp according to the invention.
Figure 10:
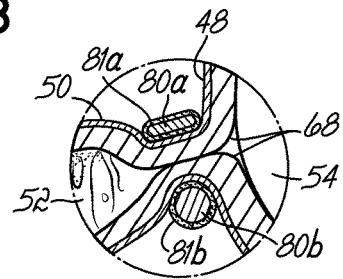
FIG. 10 is a cross sectional view illustrating the clamp of FIG. 9 applied to the left atrial appendage.

FIGS. 9 and 10 illustrate one alternative embodiment of a clamp 80 constructed in accordance with the invention. In this regard, clamp 80 may be comprised of two separate clamping portions 80a, 80b, at least one of which acts as a leaf spring member. Clamping portion 80a includes slots 82, 84 which receive respective connecting tabs 86, 88 of clamping portion 80b. In this manner, a generally oval annular shape is obtained when clamping portion 80a is connected to clamping portion 80b. Clamping portions 80a, 80b may be covered with a fabric or other suitable coating for promoting tissue ingrowth as previously described and/or for traction purposes. FIG. 9 further illustrates undulating, stamped or molded side edges 85, 87 which also may be considered projections to prevent clamp movement or migration. This may be combined with a tissue ingrowth feature as mentioned herein. Alternatively, or in addition, the clamps of this invention may have a resilient polymeric coating on one or both clamping portions to promote traction. For example, the polymeric material may be silicone.

As illustrated in FIG. 10, clamping portion 80a is flat in cross section, while clamping portion 80b is circular in cross section. This provides for more uniform and efficient force distribution along the length of clamp 80 in the closed position as shown in FIG. 10 when clamping off the left atrial appendage from the left atrium as previously described. Silicone coatings 81a, 81b are used for traction, i.e., to prevent slippage of clamp 80. The interior 52 of left atrial appendage 50 is thereby closed off completely from the left atrium 54 such that residual pockets which can trap stagnant blood are minimized or eliminated.

Figure 11:
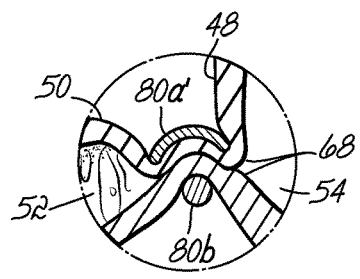
FIG. 11 is a cross sectional view similar to FIG. 10, but illustrating a clamp portion having an alternative cross sectional shape.

FIG. 11 illustrates a cross section similar to FIG. 10 but showing an alternative clamping portion 80a' which has been slightly modified to have a concave surface in cross section facing the convex outer surface of clamping portion 80b. This design can promote a better fit between clamping portion 80a' and clamping portion 80b to ensure better sealing and potentially less void space at junction 68.

Figure 12:
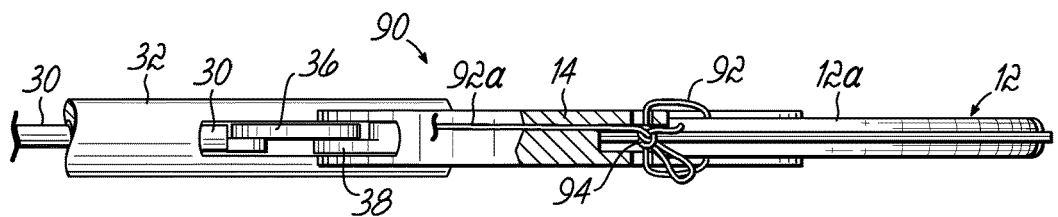
FIG. 12 is a partially cross sectioned top view of the distal end of a clamp delivery and actuation device, as well as a clamp, secured to the jaws of the device in one alternative manner.

FIG. 12 illustrates a top, partial cross sectioned view of an alternative apparatus 90 constructed in accordance with the invention. Apparatus 90 may be constructed the same as the first described embodiment in all respects except for the manner of securing clamp 12 to jaws 14, 16 (only one shown in FIG. 12). In this regard, a suture 92 is tied with a suitable slip knot 94 such that the ends 92a of suture 92 may be pulled to release clamp 12 from jaws 14, 16. It will be appreciated that a slip knot similar to slip knot 94 may be used to secure each clamping portion, although only one slip knot 94 and clamping portion 12a are shown in FIG. 12. Alternatively, suture 92 may be secured by only one slip knot 94 with a portion of the suture 92 extending around and coupling suitably with the opposite clamping portion 12b (not shown).

Figure 13:
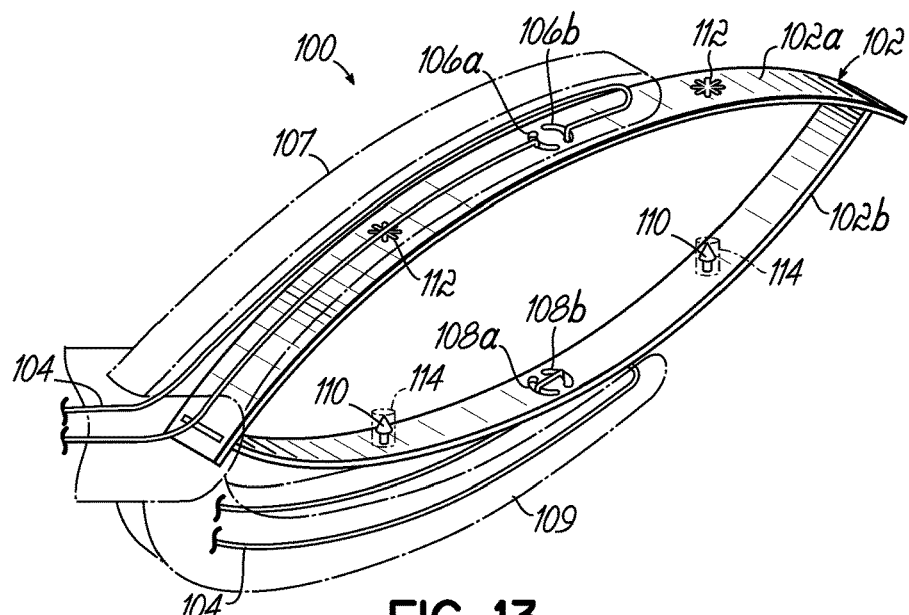
FIG. 13 is a perspective view of the distal end of a clamp delivery and actuation device, and a clamp, constructed in accordance with another alternative embodiment.
Figure 14:
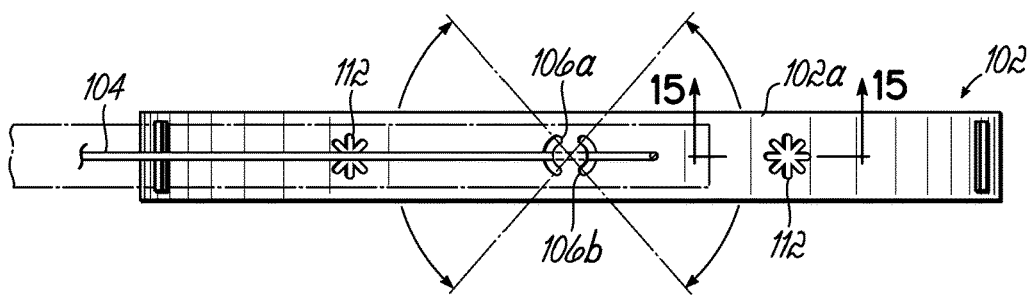
FIG. 14 is a top view of the clamp and jaw assembly shown in FIG. 13.
Figure 15:
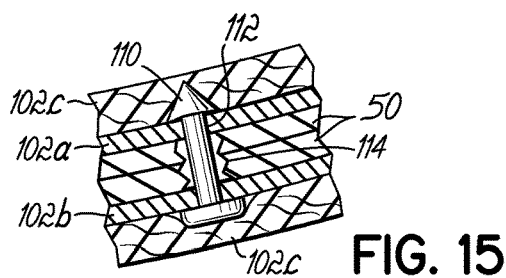
FIG. 15 is a fragmented cross sectional view illustrating the clamp of FIGS. 13 and 14 in a closed or clamping position on the left atrial appendage.

FIGS. 13-15 illustrate another alternative embodiment of an apparatus 100, again only showing the distal end of apparatus 100 in FIGS. 13 and 14. The portions not shown may be constructed and operated similarly to the previously described embodiments. In this embodiment, apparatus 100 includes a clamp 102 with first and second clamping portions 102a, 102b, which may or may not be covered with fabric, but which are illustrated as curved leaf spring members in FIGS. 13 and 14, without a fabric covering for clarity. In this embodiment, suture material 104 extends through respective curved slots 106a, 106b, 108a, 108b in each clamping portion 102a, 102b with the curved slots 106a, 106b, 108a, 108b thereby allowing for pivoting action in the jaws 107, 109 as previously described with respect to jaws 14, 16 of the first embodiment and as shown best in FIG. 14. Also in this embodiment, a plurality of projections 110 are provided on one of the clamping portions 102b and are received by respective aligned apertures 112 formed in the opposite clamping portion 102a when in the closed or clamping position as shown in FIG. 15. Collapsible sleeves 114 may be placed around the projections 110 so as to prevent snagging on tissue during delivery and application of the clamp 102 to the tissue such as the left atrial appendage 50. In this embodiment, to release the clamp 102 from the jaws 107, 109, the suture material 104 may simply be cut at the proximal end (not shown) and then carried out with the apparatus 100 after application of the clamp 102 to the tissue (appendage 50). As shown in FIG. 15, the projections 110 will extend through the fabric covering 102c, the tissue, and the receiving element or aperture 112 in this case when the clamp 102 is in the closed or clamping position. This not only assists with securing the clamp 102 in the closed position, but also further promotes tissue ingrowth as a small amount of bleeding will occur because of the penetration of the projection 110 and this bleeding can promote tissue ingrowth into the fabric covering 102c.

Figure 16:
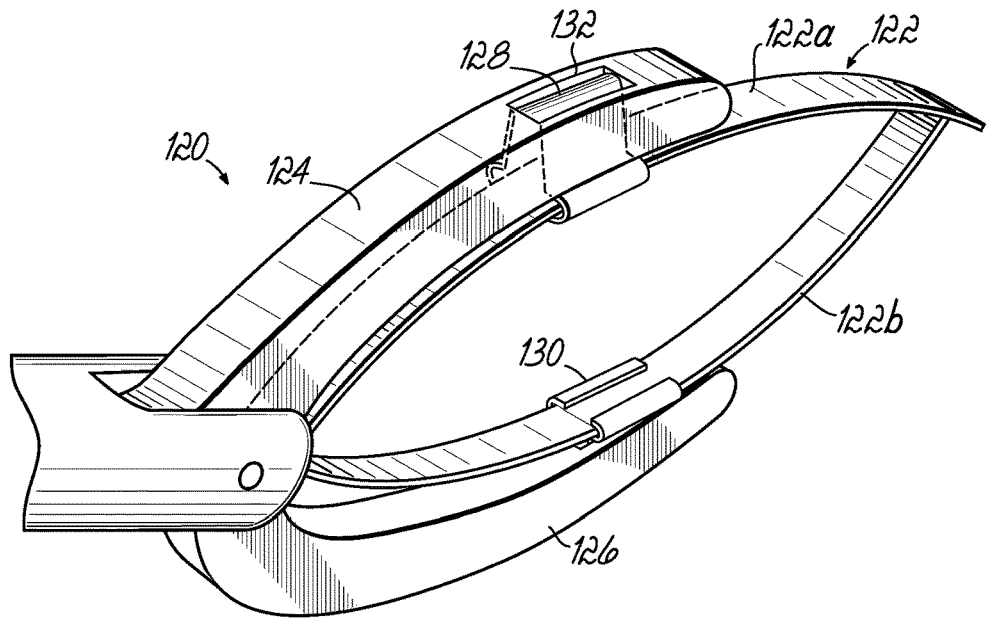
FIG. 16 is a perspective view of a clamp delivery and actuation device distal end, as well as a clamp, having a clamp retaining and releasing feature constructed in accordance with another embodiment.
Figures 17A, 17B:
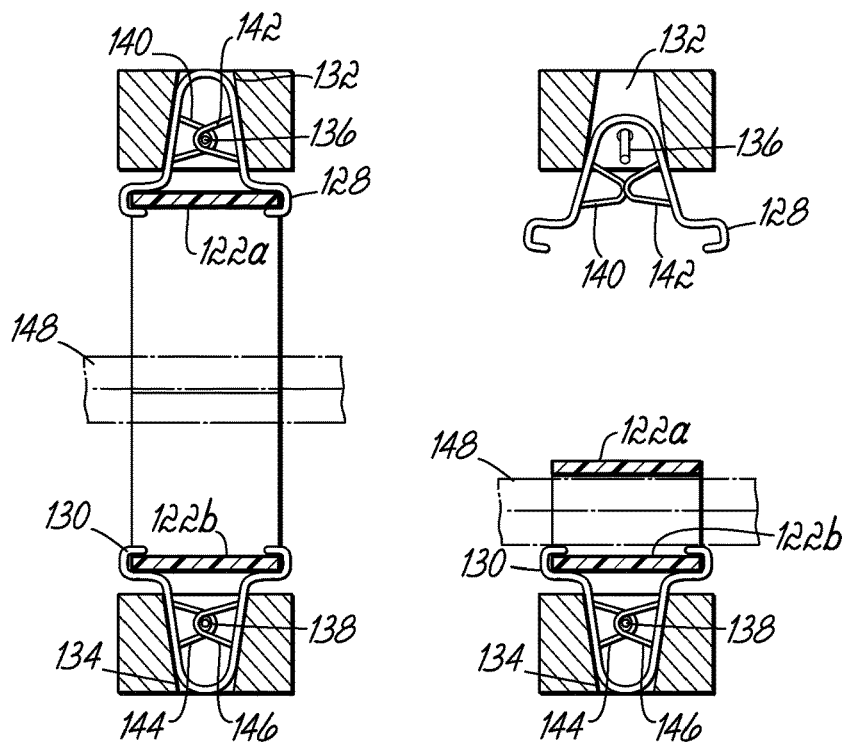
FIG. 17A is a transverse cross sectional view illustrating the clamp and gripping elements shown in FIG. 16.
FIG. 17B is a cross sectional view similar to FIG. 17A, but illustrating the release of one of the gripping elements to thereby release the corresponding clamping portion into a closed or clamping position.

FIGS. 16, 17A and 17B illustrate another alternative apparatus 120 constructed in accordance with the invention. In this embodiment, an alternative mechanism is provided for securing and releasing a clamp 122 to and from the jaws 124, 126. In this regard, gripping elements 128, 130 are provided in the form of spring loaded fingers which are normally biased to the open position shown in the upper portion of FIG. 17B. A cam-type recess 132, 134 receives each gripping element 128, 130 such that the fingers are drawn together around the respective clamping portions 122a, 122b as shown in FIG. 17A. Small diameter rods 136, 138 are placed through respective eyelets 140, 142 and 144, 146 to hold the fingers together. When rod 136 is removed from the corresponding eyelets 140, 142 as shown in the upper portion of FIG. 17B, the eyelets 140, 142 spread apart and the gripping element 128 biases itself out of the cam-type recess 132 into an open position. In this embodiment, this release may then allow the normally closed clamp 122 to assume its closed position around the tissue 148 through biased movement of clamping portion 122a toward portion 122b. Once the tissue 148 has been clamped as shown in FIG. 17B, the opposite gripping element 130 may be released from clamping portion 122b in the same manner, whereupon the apparatus 120 may be withdrawn from the patient.

Figure 18:
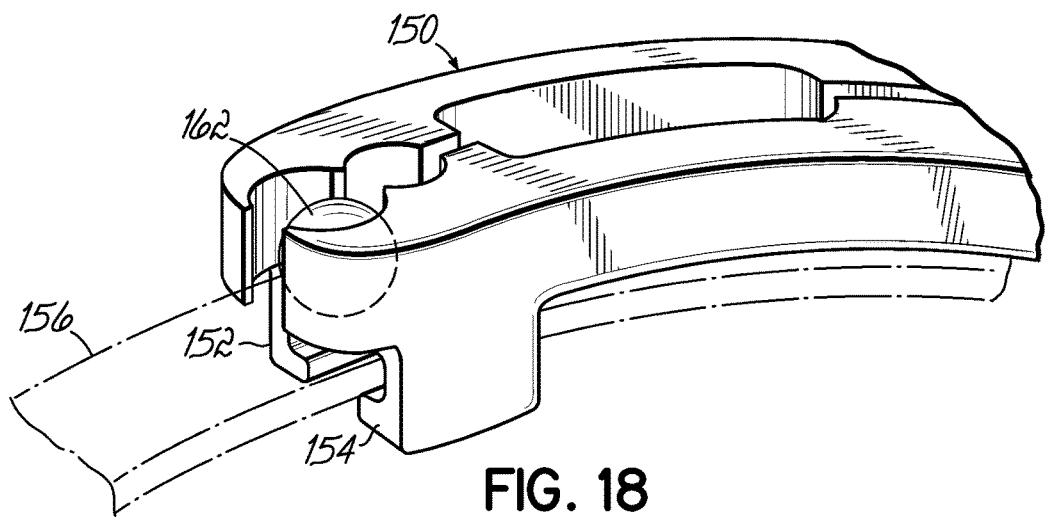
FIG. 18 is a perspective view illustrating yet another embodiment of a clamp gripping element in accordance with the invention.
Figure 18A:
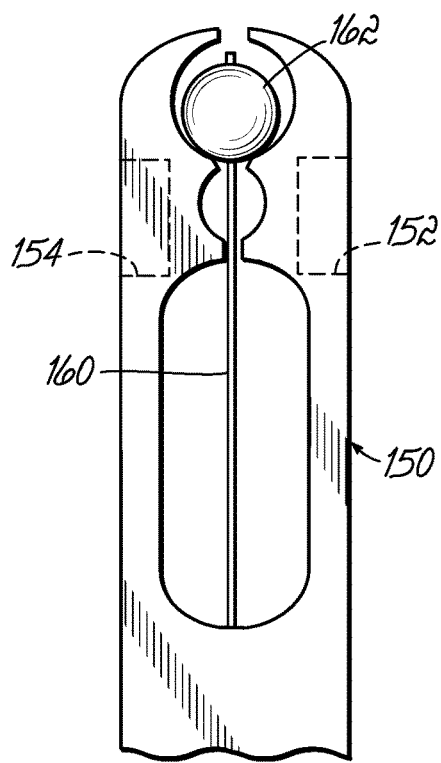
FIGS. 18A and 18B illustrate respective top views of the clamp gripping element in the closed and open positions.
Figure 18B:
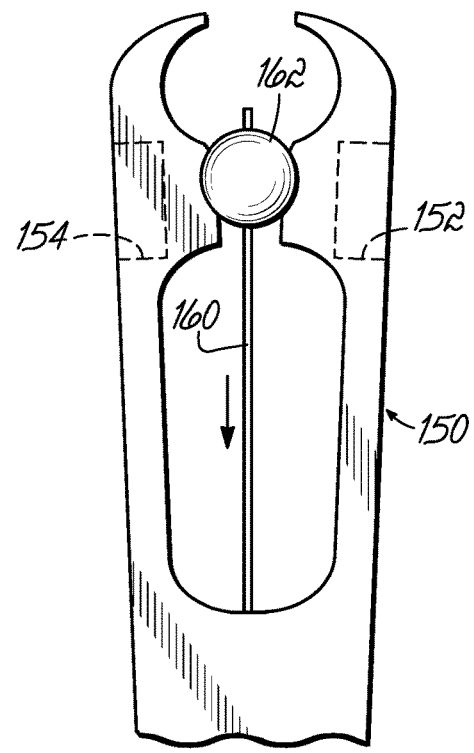

FIGS. 18, 18A and 18B illustrate another alternative clamp portion gripping element 150 having a pair of fingers 152, 154 which engage the clamping portion 156 in a manner similar to the gripping elements disclosed in FIGS. 16, 17A and 17B. As with the embodiment of FIGS. 16, 17A, and 17B, the gripping elements are carried as separate pieces on, or formed as part of, the jaws (e.g., jaws 14, 16). Fingers 152, 154 are normally closed as shown in FIG. 18A to firmly hold the clamping portion 156 therebetween, but may be opened by drawing a tension member 160 and ball or wedge member 162 rearward as shown in FIG. 18B. In this manner, one clamp portion may be released at a time in a manner similar to that described in connection with FIGS. 16, 17A and 17B. If the jaws are actuated to move one of the clamping portions to an over center position relative to the other clamping portion as previously described, then the release mechanism shown in FIGS. 18, 18A and 18B may release both clamping portions at the same time after the clamping operation has taken place.

Referring now to FIGS. 19, 19A and 20, an alternative embodiment of an apparatus 200 is shown in which like reference numerals refer to like components of the first embodiment and reference numerals having prime (') marks refer to components which have been slightly modified relative to the corresponding components in the first embodiment, as will be apparent. Apparatus 200 comprises a clamp delivery and actuation device 202 having an elongate jaw support member 27' with a clamp pivoting mechanism 204 at one end, including a rotatable actuating member 206. Rotatable actuating member 206 serves to rotate a rod (FIG. 20) back and forth via a suitable gear arrangement (not shown) or direct coupling to thereby rotate a yoke 210 back and forth. Yoke 210 is coupled with one end of clamp 12 and, therefore, rotation of yoke 210 back and forth pivots clamp 12 back and forth through a desired angle as shown in FIGS. 21A-21C. This angle may, for example, be in the range of about 10° to about 40°.

Apparatus 200, and specifically delivery and actuation device 202, includes a pistol grip handle 24' having a stationary handle portion 26' and a movable handle portion 28 coupled to stationary handle portion 26' by a pivot 32. Stationary handle portion 26' is coupled to the proximal side of pivoting mechanism 204. A stationary jaw 216 and a movable jaw 218 are coupled to the distal end of elongate jaw support member 27'. Clamp 12 is secured to jaws 216, 218 by suture material 220, 222 using a slip knot configuration as previously described such that when the exposed ends of suture material 220, 222 are pulled at the proximal end of apparatus 200, clamp 12 is released from jaws 216, 218. A link 230 is pivotally coupled to jaw 218 at a pivot 232, and jaw 218 is further pivotally coupled to elongate jaw support member 27' at a pivot 234. An actuation bar or rod 236 is pulled proximally when the surgeon squeezes handle portion 28 toward stationary handle portion 26'. This causes jaw 218 to pivot upwardly relative to stationary jaw 216 to close clamp 12 as previously described. Jaw 218 may likewise be moved away from stationary jaw 216 by moving handle portion 28 away from stationary handle portion 26' to thereby open clamp 12 if, for example, necessary to reposition clamp 12 on the tissue (not shown). As further shown in FIG. 19A, jaws 216, 218 are angled relative to the longitudinal axis of elongate jaw support member 27' by an angle y as viewed from the top. This assists with positioning clamp 12 relative to the left atrial appendage. This may also be coupled with the upward angle as shown, and as more specifically described in connection with FIGS. 8A and 8B above.

FIG. 20A illustrates an alternative embodiment which is the same as FIG. 20 but uses a yoke 210' in the shape of a closed loop instead of a forked yoke 210.

Figure 22A:
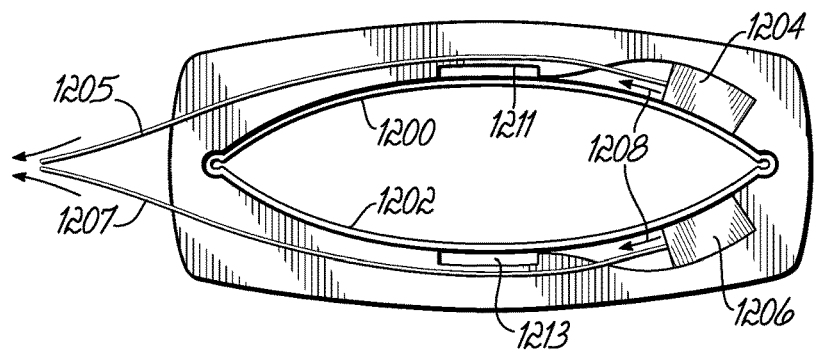
FIGS. 22A and 22B are side elevational views of another alternative clamp constructed in accordance with the invention and, respectively, shown in open and closed positions.
Figure 22B:
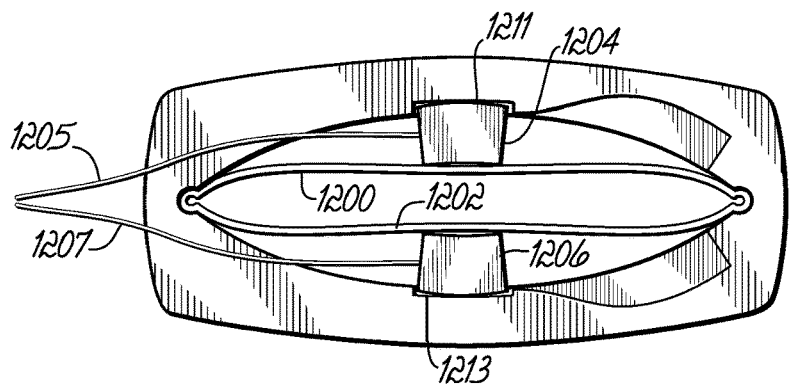
Figure 23:
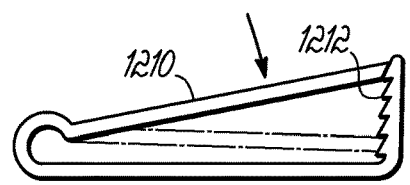
FIG. 23 is a side elevational view of another alternative clamp using ratchet elements to achieve an adjustable closed or clamping position.
Figure 24:
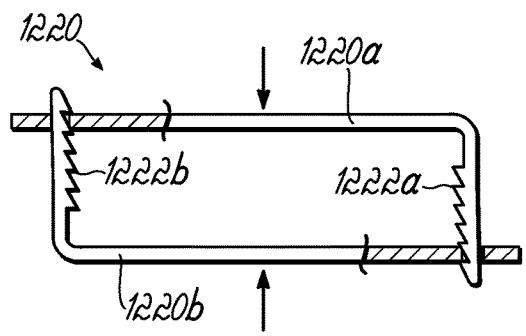
FIG. 24 is a side elevational view of another embodiment of a clamp having a two piece construction and again using ratchet elements to achieve an adjustable closed or clamping position.
Figure 25A:
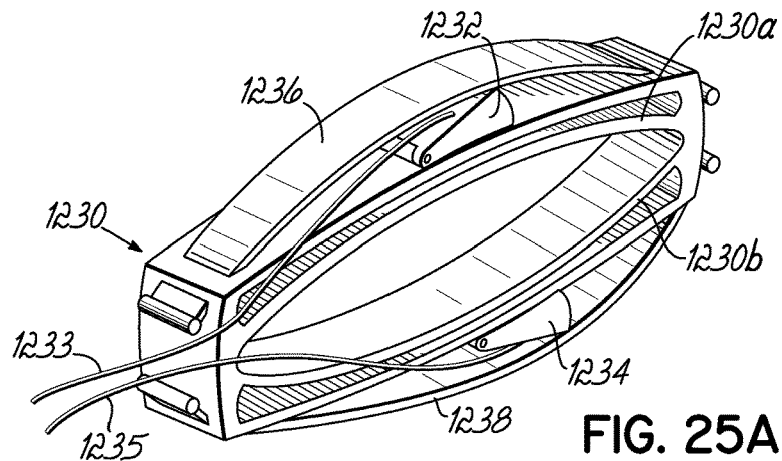
FIGS. 25A and 25B illustrate perspective views of another alternative clamp in the open and closed positions, and using a rotatable cam element to actuate the clamp into the closed position.
Figure 25B:
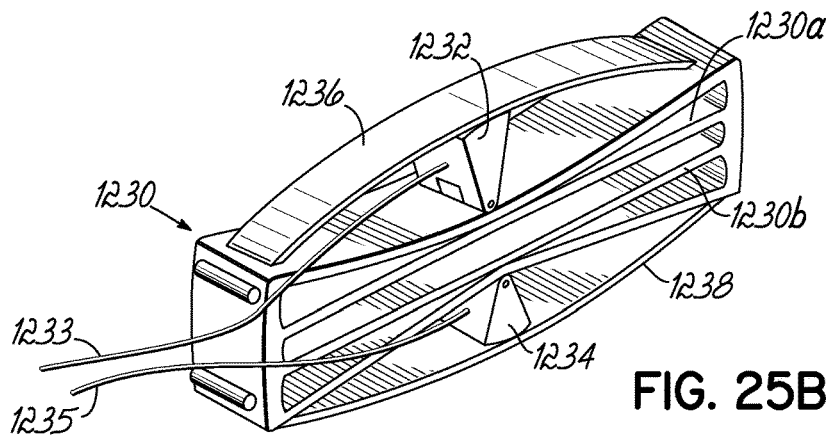
Figure 26A:
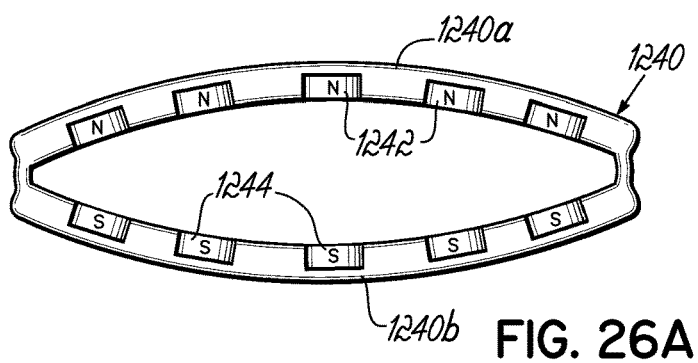
FIGS. 26A and 26B illustrate side elevational views of another alternative clamp utilizing magnetic elements to move the clamping portions between the open and closed positions.
Figure 26B:
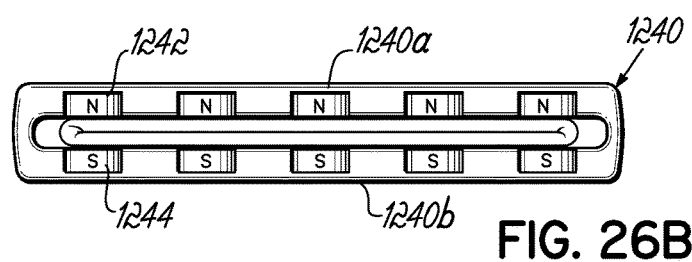
Figure 27A:
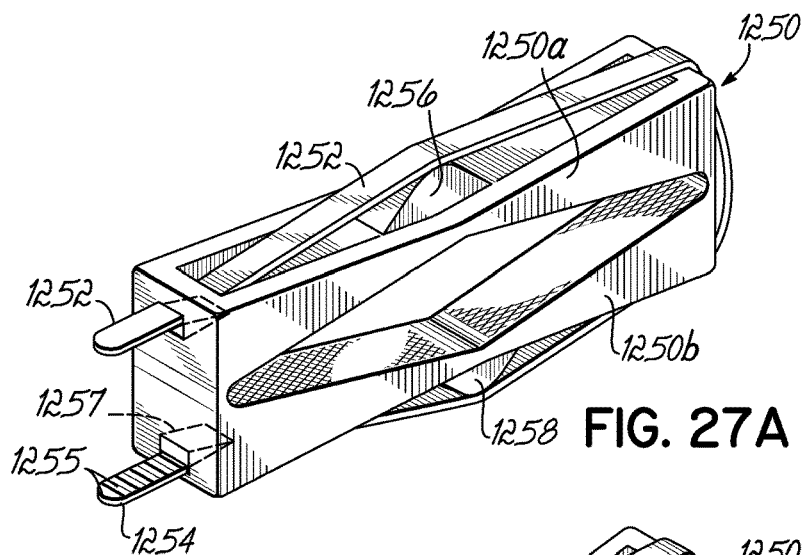
FIGS. 27A and 27B illustrate another alternative clamp, respectively, in the open and closed positions and using a linear tension element to move the clamp from the open to the closed position.
Figure 27B:
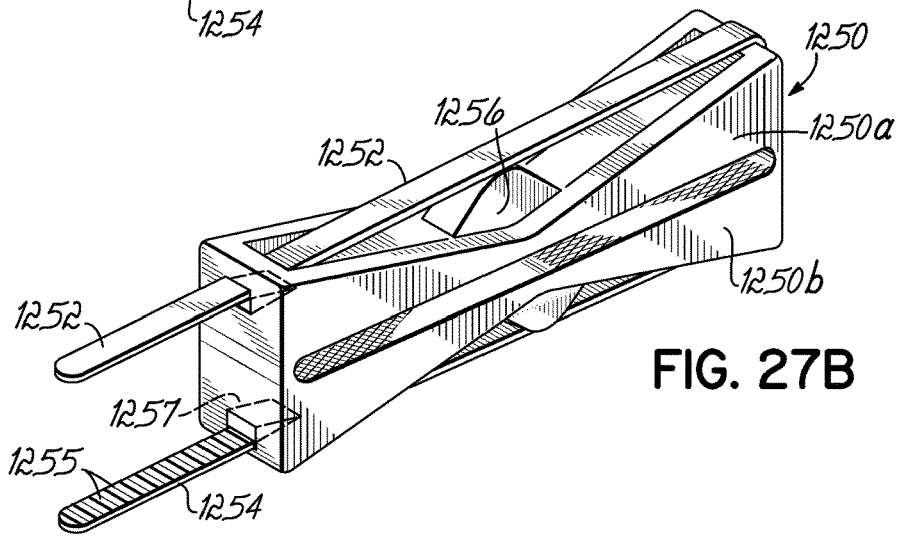
Figure 28A:
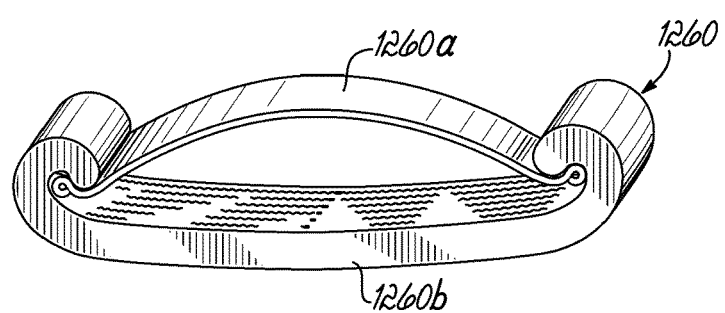
FIGS. 28A and 28B illustrate another alternative clamp, respectively, in the open and closed positions and comprised of a rigid clamping portion and a leaf spring clamping portion.
Figure 28B:
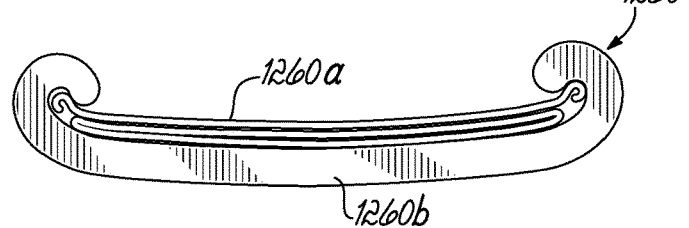

FIGS. 22A-28B illustrate various alternative clamps constructed according to the invention. More specifically, FIGS. 22A and 22B illustrate respective first and second clamping portions 1200, 1202 which may be actuated from an open position as shown in FIG. 22A, to a closed position, as shown in FIG. 22B, by sliding cam elements 1204, 1206 moving in the direction of arrows 1208 and locked in recesses 1211, 1213. This may be done by pulling tension members 1205, 1207. FIG. 23 illustrates a one piece clamp 1210 which may be moved from an open position as shown in solid lines to a closed position as shown in dash-dot lines and locked in place by respective ratchets 1212 at an appropriate clamping position. FIG. 24 is similar to FIG. 23, but illustrates a two piece clamp 1220 having first and second clamping portions 1220a, 1220b each locked in place on the other clamping portion by respective ratchets 1222a, 1222b. FIGS. 25A and 25B illustrate a clamp 1230 having first and second clamping portions 1230a, 1230b movable from the open position shown in FIG. 25A to the closed position shown in FIG. 25B. Rotatable cam elements 1232, 1234 are pivotally connected to the clamping portions 1230a, 1230b and are engageable with containment members 1236, 1238 coupled with clamping portions and having surfaces engaged with the cam elements 1232, 1234 during rotation thereof. Rotation of cam elements 1232, 1234 against containment members 1236, 1238 by pulling tension members 1233, 1235 forces the flexible clamping portions 1230a, 1230b together as shown in FIG. 25B. FIGS. 26A and 26B illustrate a clamp 1240 with respective first and second clamping portions 1240a, 1240b movable together by magnetic attraction which may, for example, be brought about by permanent magnets 1242, 1244 as shown, or by an electromagnetic device (not shown). In addition, one or both clamping portions 1240a, 1240b may act as a leaf spring as previously described. FIGS. 27A and 27B illustrate a clamp 1250 having first and second clamping portions 1250a, 1250b and activated by drawing respective tension member portions 1252, 1254 against raised elements 1256, 1258 secured to each clamping portion 1250a, 1250b. Ratchet type locking elements 1255, 1257 may be used to retain tension member portions in the clamping positions shown in FIG. 27B. FIGS. 28A and 28B illustrate another clamp 1260 comprised of a leaf spring clamping portion 1260a and a rigid clamping portion 1260b. Leaf spring 1260a may be depressed relative to rigid member 1260b whereupon it snaps into place to clamp the tissue therebetween.

Figure 29:
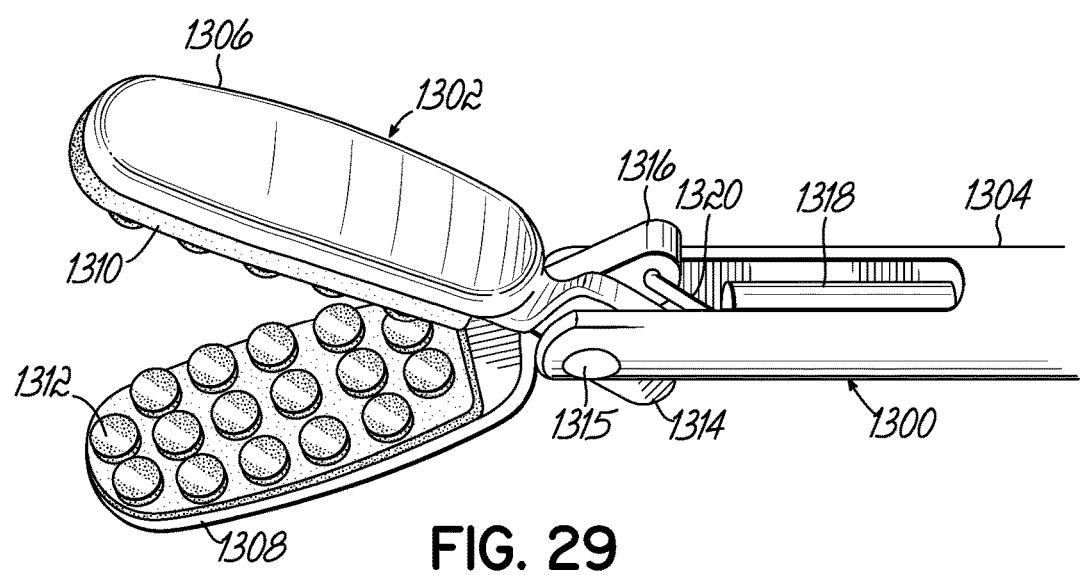
FIG. 29 is a perspective view illustrating a gripper assembly used to pull the hollow anatomical structure through a clamp constructed in accordance with the invention.

FIG. 29 illustrates the distal end of a paddle type gripper device 1300 which may be used to pull tissue, such as the left atrial appendage, through a clamp as described herein. More specifically, device 1300 includes a paddle type pivoting gripper 1302 at the distal end thereof. Gripper 1302 includes an elongate support member 1304 with first and second gripper members 1306, 1308 at the distal end, at least one of which moves toward the other to grip tissue (not shown) therebetween. In the embodiment shown, these flat paddle like gripper elements 1306, 1308 include knobbed tissue engaging surfaces 1310, 1312 to gently but firmly enable gripping of delicate tissue, such as tissue of the left atrial appendage. Gripper elements 1306, 1308 are actuated toward each other to a closed position in a manner similar to the jaws disclosed above in the first embodiment of apparatus 10. More specifically, gripper elements 1306, 1308 include proximal end portions 1314, 1316 pivoted in a scissor-type fashion to elongate support member 1304 at a pivot 1315. An actuating rod 1318 is pulled proximally, such as through the use of a pistol grip construction as previously described, and is coupled to wires 1320 (only one shown) which are respectively coupled to proximal end portions 1314, 1316. In this manner, gripper elements 1306, 1308 may be repeatedly closed and opened to gently grip and pull tissue through a clamp, such as disclosed hereinabove.

Figure 30A:
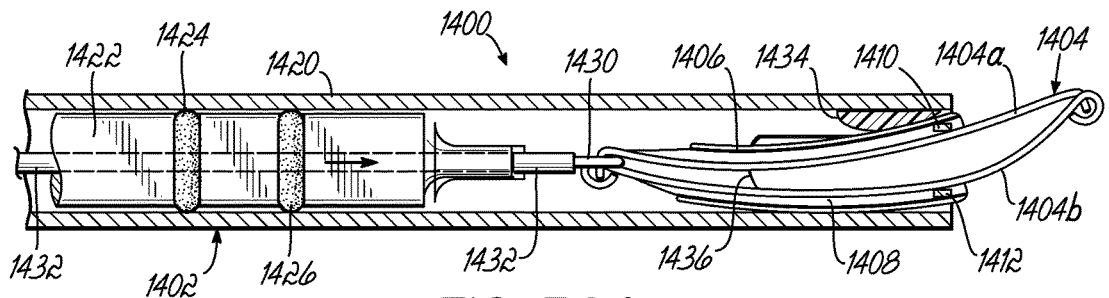
FIG. 30A is a cross sectional view illustrating the distal end of an alternative apparatus constructed in accordance with the invention including a clamp and a delivery and actuation device which may initially contain and then deploy and actuate the clamp.
Figure 30B:
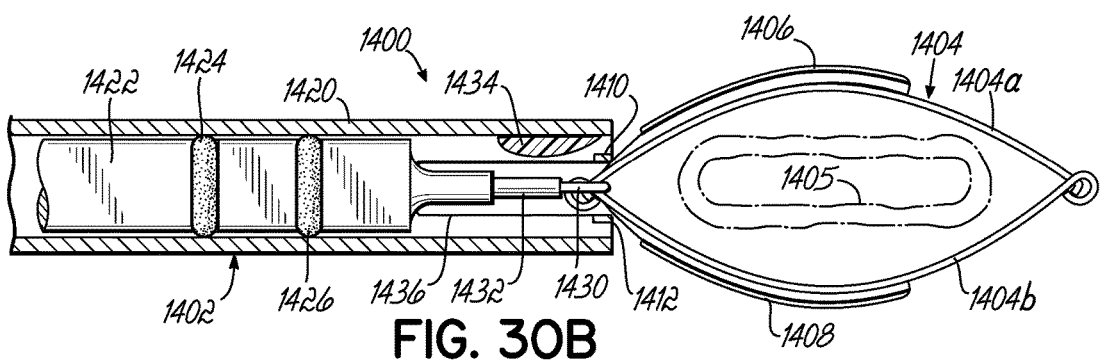
FIG. 30B is a cross sectional view similar to FIG. 30A, but illustrating the clamp fully deployed into an open position around a hollow anatomical structure.
Figure 30C:
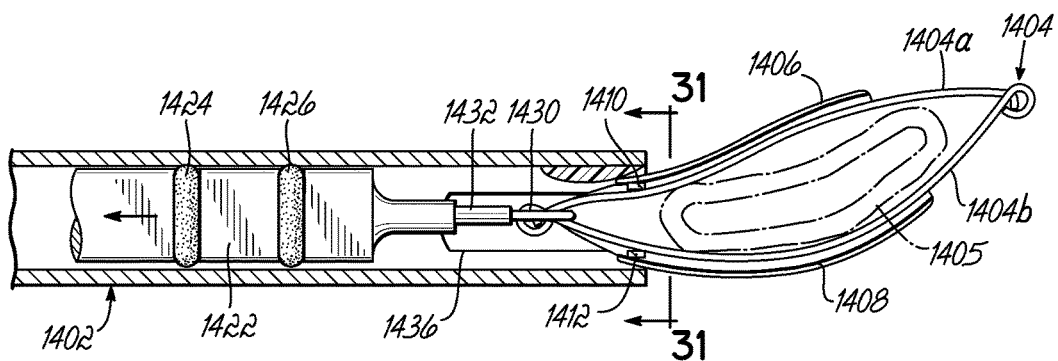
FIG. 30C is a cross sectional view similar to FIG. 30B, but illustrating the clamp actuating procedure employed by retracting the clamp into the delivery and actuation device.
Figure 31:
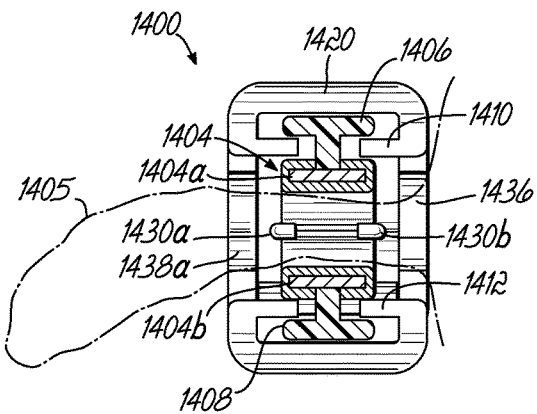
FIG. 31 is a cross sectional view taken along line 31-31 of FIG. 30C.
Figure 32A:
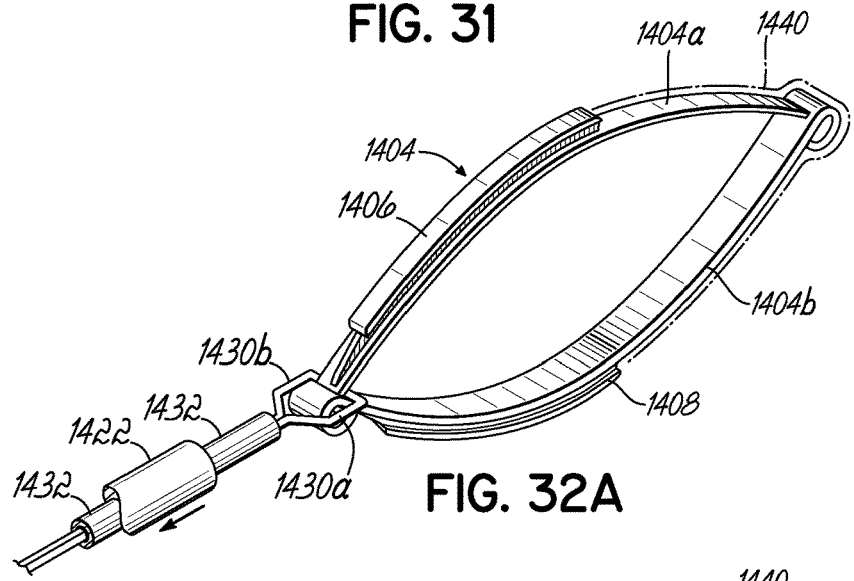
FIGS. 32A and 32B are perspective views illustrating respective engaged and disengaged positions of the delivery and actuation device and the clamp.

Referring to FIGS. 30A-30C, an apparatus 1400 is shown and includes a clamp delivery and actuation device 1402 configured to internally carry, deploy and then actuate a clamp 1404 onto a hollow anatomical structure 1405. Clamp 1404 includes respective clamping portions 1404a, 1404b having respective rails 1406, 1408 carried thereon, such as by being integrally molded therewith or otherwise secured thereto. Rails 1406, 1408 ride on respective guide members 1410, 1412, as best shown in FIG. 31, for purposes as will be described. Device 1402 includes a tube 1420 which may have a diameter sized for minimally invasive surgery (e.g., 8 mm) and which carries a first rod or clamp deployment member 1422 preferably in the form of a piston-type member which reciprocates within the interior of tube 1420. O-rings 1424, 1426 or similar elements may be used to provide some frictional resistance and better control to the reciprocating motion of rod 1422. A gripper 1430 is carried for reciprocating movement with rod 1422 and is used to grasp clamp 1404 as shown in FIGS. 30A-30C, as well as in FIGS. 31 and 32A. A tube 1432 is also carried by rod 1422 and holds gripper 1430. Tube 1432 may be used to open and close gripper elements 1430a, 1430b (FIGS. 31, 32A-B) and also to push clamp 1404 out of tube 1420 during deployment of clamp 1404 as described below. As further shown in FIG. 32B, when tube 1432 is retracted, or pulled to the left with respect to gripper 1430, gripper elements 1430a, 1430b will spring apart into their normally biased open or disengaged position. At this point, clamp 1404 may be disengaged from delivery and actuation device 1402. Pushing tube 1432 in the opposite direction into the position shown in FIG. 32A will close gripper elements 1430a, 1430b. It will be appreciated that other manners of securing clamp 1404 for movement with respect to device 1402 may be used instead.

Figure 30D:
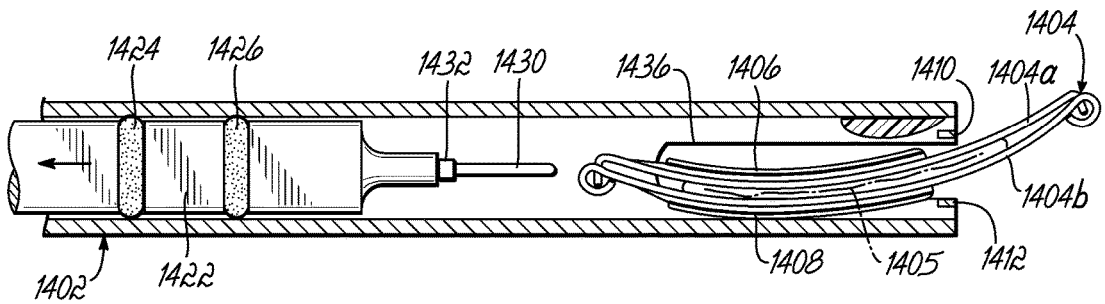
FIG. 30D is a cross sectional view similar to FIG. 30C, but illustrating the clamp in its fully clamped or closed position on the hollow anatomical structure.
Figure 32B:
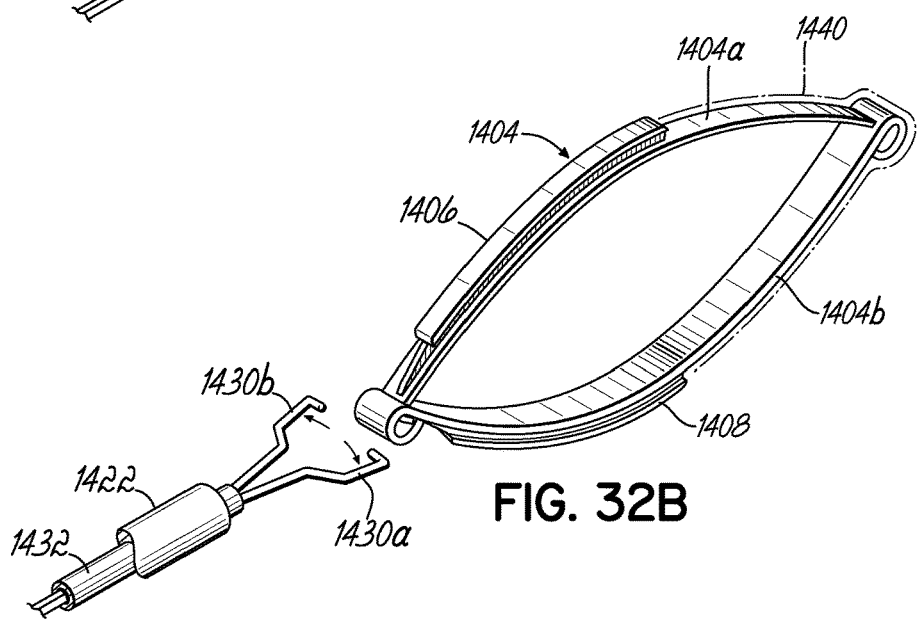

More specifically referring to FIG. 30A, clamp 1404 may be initially fully contained within tube 1420, in a closed position, although FIG. 30A shows clamp 1404 partially deployed. As clamp 1404 is pushed entirely out of the distal end of tube 1420, the clamp will be opened as shown in FIG. 30B since the path along which the rails 1406, 1408 move along guides 1410, 1412 forces clamping portion 1404a past an over-center position at which clamping portion 1404a will snap into the open position shown. The combined delivery and actuation device 1402 and clamp 1404 may be initially delivered in a compact state through a small incision in the patient. Once the distal end of apparatus 1400 is inserted in this fashion, deployment may take place as shown in FIG. 30B and described above. Once the hollow anatomical structure 1405 is positioned between clamping portions 1404a, 1404b as shown in FIG. 30B, clamp 1404 may be withdrawn into tube 1420. A compression member 1434 will deform clamping portion 1404a past an over-center position toward the closed position whereupon clamping portion 1404a will snap into the closed position shown in FIG. 30D. At this point, tube 1432 may be retracted to the left as shown in FIGS. 30D and 32B thereby releasing gripper 1430. As slots 1436, 1438 (FIG. 31) are formed on opposite sides of tube 1420, the hollow anatomical structure 1405 may be initially retracted into tube 1420 during the clamping process. As rails 1406, 1408 disengage their respective guide members 1410, 1412 as shown in FIG. 30D, delivery and actuation device 1402 may be withdrawn from the patient leaving the clamp 1404 and hollow anatomical structure 1405 in place. As further shown in dash-dot lines in FIGS. 32A and 32B, clamp 1404 may have a fabric covering 1440 which, preferably, is adapted to promote tissue ingrowth as previously discussed. This embodiment is especially adapted for use in minimally invasive surgical procedures. For such purposes, the maximum outer diameter of tube 1420 is preferably about 12 mm, although various cross sectional shapes may be used having outer diameters from, for example, about 8 mm to about 12 mm.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known.

What is claimed is:

1. A method of occluding an appendage of the heart with a clamp having at least first and second elongate clamping portions configured to be implanted and placed on opposite sides of the left atrial appendage, at least one of the first and second clamping portions being movable toward the other of the first and second clamping portions from an open position into a clamping position to occlude the left atrial appendage, and having first and second ends spaced apart from each other along a longitudinal direction of the clamp, the first and second clamping portions joined together proximate the first and second ends, whereby the first and second clamping portions and the first and second ends define a closed shape, and a fabric covering on the first and second clamping portions, the fabric covering extending completely around an outer peripheral surface of each of the first and second clamping portions and the first and second ends, the method comprising:

implanting the clamp by positioning the first and second elongate clamping portions on opposite sides of the appendage;

biasing at least one of the first or second elongate clamping portions toward the other of the first and second elongate clamping portions to place the clamp from the open position into the clamping position on the appendage and thereby occlude the appendage; and promoting tissue ingrowth into the fabric to retain the clamp in place on the appendage.

2. The method of claim 1, wherein the method further comprises:

accessing the appendage of the heart through an intercostal space of a patient.

3. The method of claim 1, further comprising:

moving at least one of the first and second elongate clamp portions away from the other of the first and second elongate clamping portions;

repositioning the clamp on the appendage; and moving at least one of the first or second elongate clamping portions toward the other of the first and second elongate clamping portions to occlude the appendage.

4. The method of claim 1, further comprising:

delivering the clamp in proximity to the appendage with a delivery device; and pivoting the clamp with respect to the delivery device prior to occlude the appendage.

5. The method of claim 1, further comprising:

engaging the appendage on opposite sides with straight line contact between the first and second elongate clamping portions and the opposite sides of the appendage.

6. The method of claim 1, wherein biasing at least one of the first or second elongate clamping portions further comprises:

using a biasing element positioned proximate each of two opposite ends of the first and second elongate clamping portions to bias the first and second elongate clamping portions toward each other and against the opposite sides of the appendage.

7. The method of claim 1, further comprising:

attaching the clamp to a delivery device;

delivering the clamp in proximity to the appendage with the delivery device; and detaching the clamp from the delivery device.

* * * * *